(12) United States Patent
Gaisford et al.

(10) Patent No.: US 6,316,759 B2
(45) Date of Patent: *Nov. 13, 2001

(54) MICROWAVE HEATING APPARATUS FOR GAS CHROMATOGRAPHIC COLUMNS

(75) Inventors: Gregory Scott Gaisford, Denver; David L. Walters, Fort Collins, both of CO (US)

(73) Assignee: MT Systems, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/729,134

(22) Filed: Dec. 1, 2000

Related U.S. Application Data

(63) Continuation-in-part of application No. 09/359,879, filed on Jul. 23, 1999, now Pat. No. 6,157,015, which is a continuation-in-part of application No. 09/262,230, filed on Mar. 4, 1999, now Pat. No. 6,093,921.

(51) Int. Cl.[7] .............................. H05B 6/80; H05B 6/72; G01N 30/02
(52) U.S. Cl. ..................... 219/748; 219/750; 219/679; 73/23.35; 95/87; 422/21
(58) Field of Search ..................................... 219/745, 746, 219/748, 749, 750, 679, 678, 690, 695, 696, 686; 73/23.35; 95/82, 87; 422/89, 21

(56) References Cited

U.S. PATENT DOCUMENTS

| | | |
|---|---|---|
| 3,023,835 | 3/1962 | Brashear . |
| 3,169,389 | 2/1965 | Green, Jr. et al. . |
| 3,232,093 | 2/1966 | Burow et al. . |
| 3,527,567 | 9/1970 | Philyaw et al. . |
| 4,204,423 | 5/1980 | Jordan . |
| 4,339,648 | 7/1982 | Jean . |
| 4,347,216 | 8/1982 | Kawasaki et al. . |
| 4,861,556 | 8/1989 | Neas et al. . |
| 4,882,286 | 11/1989 | Neas et al. . |
| 4,904,450 | 2/1990 | Floyd . |
| 4,923,486 | 5/1990 | Rubey . |
| 5,005,399 | 4/1991 | Holtzclaw et al. . |
| 5,009,099 | 4/1991 | Wells et al. . |
| 5,022,756 | 6/1991 | Rhodes . |
| 5,028,243 | 7/1991 | Rubey . |
| 5,066,843 | 11/1991 | Revesz . |
| 5,114,439 | 5/1992 | Yost et al. . |
| 5,131,993 | 7/1992 | Suib et al. . |
| 5,314,664 | 5/1994 | Sperling et al. . |

(List continued on next page.)

*Primary Examiner*—Philip H. Leung
(74) *Attorney, Agent, or Firm*—Dorr, Carson, Sloan & Birney, P.C.

(57) ABSTRACT

A microwave heating apparatus is used for heating a chromatographic column assembly containing a microwave absorbing material. The microwave heating apparatus includes an antenna transmitting a microwave signal and a resonant cavity containing the chromatographic column assembly. The chromatographic column assembly extends relative to predetermined electromagnetic field strength contours within the resonant cavity to provide a predetermined heating profile along the length of the chromatographic column assembly. For example, a single-mode chromatographic column microwave oven can be used to heat a coiled chromatography column to a desired temperature gradient along its length. Oven design embodiments utilizing coaxial transmission line structures, coaxial resonators, and cylindrical resonators are described. Oven designs are provided to achieve more suitable oven size for fixed operating frequencies. Apparatuses for impedance matching an oven to a microwave source are described. Finally, designs providing for rapid column cool down and improved control of the column thermal environment are described.

17 Claims, 18 Drawing Sheets

U.S. PATENT DOCUMENTS

| | | |
|---|---|---|
| 5,377,426 | 1/1995 | Pare . |
| 5,427,741 | 6/1995 | Bennett . |
| 5,443,795 | 8/1995 | Revesz . |
| 5,447,052 | 9/1995 | Delaune et al. . |
| 5,471,037 | 11/1995 | Goethel et al. . |
| 5,519,947 | 5/1996 | Pare et al. . |
| 5,589,630 | 12/1996 | Weigand et al. . |
| 5,611,846 | 3/1997 | Overton et al. . |
| 5,663,488 | 9/1997 | Wang et al. . |
| 5,675,909 | 10/1997 | Pare . |
| 5,744,696 | 4/1998 | Wang et al. . |
| 5,808,178 | 9/1998 | Rounbehler et al. . |
| 6,093,921 * | 7/2000 | Giasford et al. .................... 219/748 |
| 6,157,015 * | 12/2000 | Giasford et al. .................... 219/748 |

* cited by examiner

TM010 Resonator

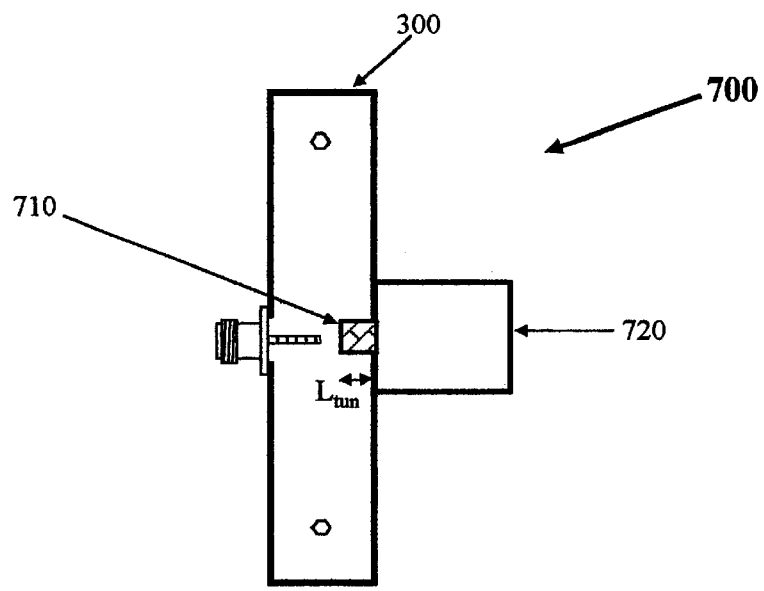
Figure 20
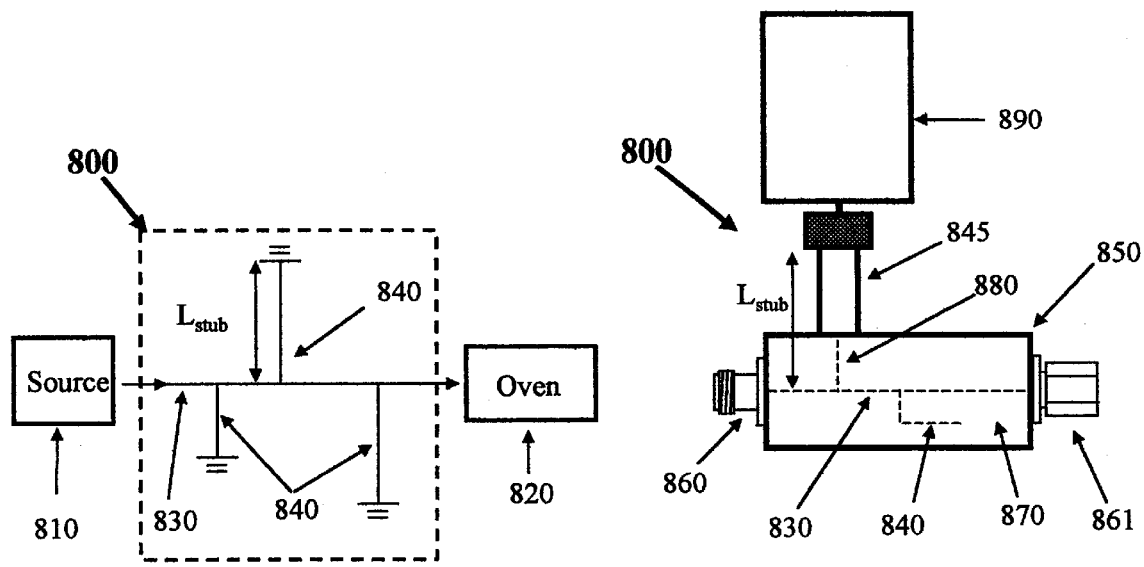
Figure 21a
Figure 21b

MICROWAVE HEATING APPARATUS FOR GAS CHROMATOGRAPHIC COLUMNS

RELATED APPLICATIONS

The present application is a continuation-in-part of the Applicants' U.S. patent application Ser. No. 09/359,879, entitled "Microwave Heating Apparatus For Gas Chromatographic Columns," filed on Jul. 23, 1999 now U.S. Pat. No. 6,157,015, which is a continuation-in-part of U.S. patent application Ser. No. 09/262,230, filed on Mar. 4, 1999, now U.S. Pat. No. 6,093,921, issued on Jul. 25, 2000.

BACKGROUND OF THE INVENTION

1. Field of the Invention

The invention relates generally to the field of gas chromatography and specifically to the design of microwave heating apparatuses for heating a chromatographic column.

2. Statement of the Problem

Gas chromatography is a physical method for the separation, identification, and quantification of chemical compounds. This method is used extensively for applications that include the measurement of product purity in analytical chemistry, the determination of environmental contamination, the characterization of natural substances, and the development of new products and processes.

A sample mixture to be analyzed in a gas chromatograph (GC) is injected into a flowing neutral carrier gas stream and the combination then flows through the chromatographic column. The inner surface of the column is coated with a material called the stationary phase. As the sample mixture and carrier stream flow through the column, the components within the mixture are retained by the stationary phase to a greater or lesser degree depending on the relative volatility of the individual components and on their respective affinities for the stationary phase. When the individual mixture components are released into the carrier stream by the stationary phase, they are swept towards the column outlet where they are detected and measured with a detector. Different chemical compounds are retained for different times by the stationary phase. By measuring the retention times, the specific compounds in the mixture can be identified. The relative concentration of the compounds is determined by comparing the peak amplitudes measured with the detector for each compound.

GC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatograph.

Attempts to localize the resistive heat element onto the column itself so as to reduce or eliminate peripheral heating of the 'oven' are described in U.S. Pat. Nos. 3,169,389 (Green et al.), 3,232,093 (Burow et al.), 5,005,399 (Holtzclaw et al.), and 5,808,178 (Rounbehler et al.). Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column or in the environment around the heating element. Uneven heating of the column in turn compromises the quality of the analysis.

Alternative methods for heating chromatographic columns by means of microwave heating are described in U.S. Pat. No. 4,204,423 (Jordan) and U.S. Pat. No. 5,808,178 (Rounbehler et al.). Potential advantages of microwave heating are selectivity, efficiency and speed. Suitable objects placed in a microwave oven will be heated when the oven is operated, but the oven itself will not be heated. Microwave heating occurs in materials which absorb microwave energy and convert it into heat. Thus, chromatographic columns or column assembles which contain appropriate microwave absorbing materials will be selectively heated in a microwave oven while leaving the oven itself cool. Selective microwave heating makes possible more efficient heating because most thermal energy is transferred directly to the object to be heated. As compared to existing GC ovens, faster heating and cooling is also possible with microwave heating because less material is heated.

In order to heat a material in a microwave oven, the material must absorb microwave energy at least in part. Standard GC capillary columns are made of fused silica and polyimide. Neither of these materials absorb microwave energy appreciably. Consequently, these columns cannot be heated in a microwave oven in the manner taught by Jordan. The Applicants' U.S. Pat. Nos. 5,939,614 and 6,029,498 entitled "Chromatography Column For Microwave Heating", address this limitation. They describe the design of chromatographic columns incorporating microwave absorbing material facilitating microwave heating.

Common capillary gas chromatographic columns range in size from 0.1 to 0.53 mm in internal diameter and from 4 to 60 meters in length. Chromatographic columns are usually quite flexible, especially fused silica capillary columns. These columns can readily be coiled up into compact circular bundles having diameters as small as several centimeters (though other bundle shapes with appropriate bend radii can also be made). In coiled form, a chromatographic column can be heated within a microwave oven of practical size so that a desired temperature profile is achieved along the length of the column.

There is another fundamental limitation in the method taught by Jordan. He does not describe any specific oven design in which a chromatographic column can be heated in a useful manner. To function properly, a GC column must not only be heated, it must be heated precisely. The temperature profile along the length of the column must be controlled within tight tolerances. For most applications in existing chromatographic ovens, the column temperature is kept essentially constant along its length, i.e. isothermally, except for the ends that are usually maintained at a higher temperature.

To achieve a desired temperature profile along the length of a coiled GC column with microwave heating, the microwave heating apparatus must be specifically designed to expose the coiled column to a specific electromagnetic field gradient along the column length. This is only achievable with a properly designed microwave heating apparatus and not with a generic microwave oven. Jordan does not describe how to design a microwave heating apparatus in which the electromagnetic field distribution is controlled in such a manner that a GC column is heated to a desired temperature profile. The term "profile" is used herein to refer to the temperature versus position along the length of the column at a fixed point in time, as opposed to the temperature of the column as a function of time.

To isothermally heat a chromatographic column having a fixed microwave loss factor along its length in a microwave oven requires that the column must be exposed to the same electromagnetic field strength over its entire length such that the whole of the column absorbs equal thermal energy and thus remains at the same temperature. This cannot be achieved with conventional box-like, rectilinear, multi-mode microwave ovens where the electromagnetic field varies in an extremely complex manner throughout the oven volume. It can only be achieved with a microwave oven specifically designed to heat a chromatographic column.

3. Solution to the Problem

There are three essential features of a useful microwave oven to be used for heating coiled chromatographic columns: (1) The oven should be a substantially single mode oven within which the electromagnetic field is predictable; (2) The electromagnetic field within the oven must have smoothly varying, continuous isofield lines oriented about a central axis such that individual coils of the column bundle can physically trace a path along or around the isofield lines resulting in a desired temperature gradient in each column coil; and (3) The electromagnetic field strength must vary from one coil to the next in the bundle by an increment sufficient to achieve the desired temperature gradient from one coil to the next.

The simplest column bundle geometry is that of a circular helix wherein each column coil is lined up adjacent to the next such that the overall bundle shape is that of a thin walled, constant diameter cylinder. To heat such a column bundle isothermally assuming the microwave absorption characteristics of the bundle do not significantly vary along the length of the column, the electromagnetic field strength must be equal (or nearly so) at all points in the cylindrical surface formed by the coiled column. Therefore, the electromagnetic field must be radially symmetric (rotationally invariant) and axially invariant. A microwave oven capable of generating such a field must itself be radially symmetric, i.e., circular in cross-section. Axially, it must be constructed to establish an equal electromagnetic field strength along in the length of the column bundle.

The present invention describes a number of chromatographic column microwave oven embodiments which can be used for heating chromatographic columns. A preferred embodiment of the oven is single mode resonant cavity and specifically a $TM_{010}$ cylindrical resonant cavity. This cavity can be tuned to deliver virtually all available microwave power to the column heating element.

SUMMARY OF THE INVENTION

The present invention provides a microwave oven for heating coiled chromatographic columns to a desired temperature profile. To achieve a specific column temperature profile, the chromatographic column microwave oven establishes: (1) an electromagnetic field characterized by smoothly varying, continuous isofield lines oriented about a central axis such that individual column coils of a column bundle can physically trace a path along or around the isofield lines resulting in a desired temperature profile in each column coil; and (2) a controlled electromagnetic field gradient from one coil of the column bundle to the next so the desired temperature gradient is established from one coil to the next and thus along the whole of the column. Oven design variations include coaxial transmission line structures, coaxial resonators, and cylindrical resonators. A preferred oven design uses a cylindrical resonant cavity structure which is tuned to deliver the maximum amount of available microwave energy into the cavity.

It is the object of the invention to provide a chromatographic column microwave oven capable of faster heating and cooling rates than with conventional column ovens.

It is the object of the invention to provide a chromatographic column microwave oven for which it is possible to maximize the efficiency of power delivery to the column.

It is the object of the invention to provide an extremely small chromatographic column oven.

It is the object of the invention to provide a chromatographic column microwave oven for which size can be adjusted even if the operating frequency is fixed.

It is the object of the invention to provide a chromatographic column microwave oven with an adjustable resonant frequency.

It is the object of the invention to provide a chromatographic column microwave oven with adjustable input impedance.

It is the object of the invention to provide a chromatographic column microwave oven within which a chromatographic column can be cooled evenly.

It is the object of the invention to provide a chromatographic column microwave oven for which it is possible to regulate the temperature of the oven walls.

BRIEF DESCRIPTION OF THE DRAWINGS

The present invention can be more readily understood in conjunction with the accompanying drawings, in which:

FIG. 20 shows a chromatographic column microwave oven system that uses a frequency tuning element to adjust the resonant frequency of the oven.

FIG. 21a shows an electrical diagram of a stub tuner.

FIG. 21b shows a coaxial embodiment of a stub tuner that can be used with a chromatographic column microwave oven.

DETAILED DESCRIPTION OF THE INVENTION

Figure 1:
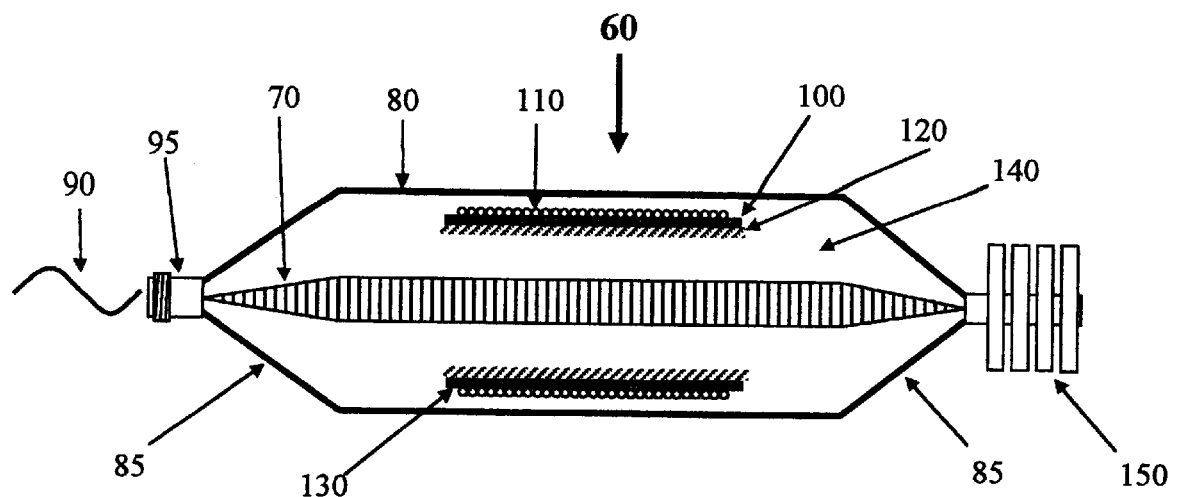
FIGS. 1 and 2 are two orthogonal cross-sectional views of a chromatographic column microwave oven wherein the oven is a coaxial transmission line.

Potential advantages to be derived from heating chromatographic columns in microwave ovens are heating selectivity, efficiency, and speed. Suitable objects placed in a microwave oven will be heated when the oven is operated, but the oven itself will not be heated. In the descriptions of microwave ovens for chromatographic column described herein, the term "microwave" is used broadly to refer to electromagnetic radiation in the frequency range from 10 MHz to 100 GHz.

Microwave heating occurs in materials that absorb microwave energy and convert it into heat. Thus, chromatographic columns or column assembles which contain appropriate microwave absorbing materials will be selectively heated in a microwave oven while leaving the oven itself cool. Selective microwave heating makes possible more efficient heating because most thermal energy is transferred directly to the object to be heated. In addition, faster heating and cooling is possible because much less material is heated.

Conventional microwave ovens are typically closed metal boxes of at least a cubic foot in volume within which the electromagnetic energy is confined. They operate at 2.45 GHz at which the wavelength of electromagnetic waves is about 4.82 inches. A conventional microwave oven acts as a multi-mode resonant cavity. A resonant cavity is a structure within which the interference pattern between multiply reflecting electromagnetic waves excited in the cavity resolves itself into a well defined and stable standing wave pattern. A multi-mode resonant cavity is one in which many different and unique standing wave patterns can exist. A conventional microwave oven can support a very large number of modes because the internal dimensions of the oven are many times the wavelength. The result is a complex, intermingled pattern of overlapping standing wave patterns from different resonant modes. At some points the electromagnetic field strength is high and at other points the field strength is zero. Objects heated in such complex electromagnetic fields are heated in similarly complex and uneven patterns. The spacing between adjacent hot spots is typically less than one wavelength. Manufacturers of such ovens attempt to smooth out the temperature distributions of materials heated in the ovens with: (1) mode stirrers (e.g., metal fans) to stir the mode pattern in the oven; and (2) rotating platforms to physically move material around in the oven while it heats. These methods provide only modest improvements in the electromagnetic field profile to which material is exposed in conventional microwave ovens.

Most gas chromatographs heat chromatographic columns isothermally, except for the ends which are kept hotter by the injector and detector assemblies (i.e., the temperature of the central length of the column is kept at the same value). To isothermally heat a chromatographic column having a constant loss factor along its length in a microwave oven requires that the column must be exposed to the same electromagnetic field strength over its entire length, such that the whole of the column absorbs equal thermal energy and is thus kept at isothermal conditions.

The most common type of chromatographic column used in gas chromatographs is the fused silica capillary column. These columns typically range in size from 0.1 to 0.53 mm in internal diameter and from 4 to 60 meters in length. Most chromatographic columns are quite flexible, especially fused silica capillary columns. These columns can readily be coiled up into compact circular bundles having diameters as small as several centimeters (though other bundle shapes with appropriate bend radii can also be made). Even with such a small column bundle, a conventional consumer microwave oven cannot be used to heat the column bundle isothermally. Even a bundle as small as two centimeters in diameter would be exposed to an electromagnetic field gradient so large as to produce great variation in temperature along the column length.

A more fundamental flaw with conventional microwave ovens is that they are box-like. Box-like resonant cavities tend to generate field distributions symmetrical in rectangular coordinates. Constant field strength contour lines (which herein will be called isofield lines) thus tend to be rectilinear. Existing chromatographic columns cannot be bent into tight rectangular shapes, however, so they cannot be made to trace the rectilinear isofield lines, making isothermal heating impossible. Consequently, non-rectangular oven geometries are preferred with currently available chromatographic columns.

Coaxial Chromatographic Column Microwave Ovens

Figure 2:
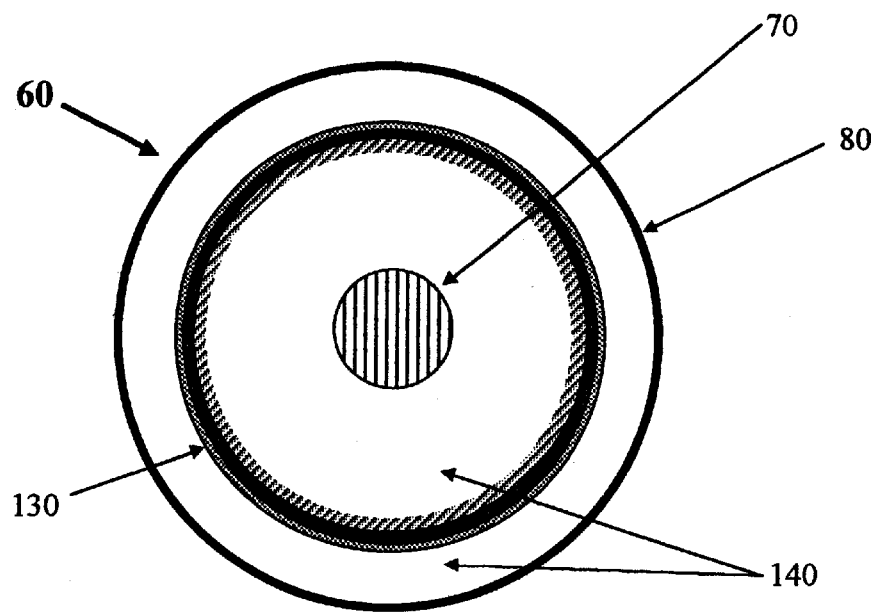

FIGS. 1 and 2 show two orthogonal cross-sectional views of one embodiment of a cylindrically shaped chromatographic microwave oven 60. The oven 60 is a coaxial transmission line structure. FIG. 1 shows a cross sectional view along the central axis of the chromatographic microwave oven 60. FIG. 2 shows the radial cross section perpendicular to the central axis in the middle of the oven 60.

A microwave signal 90 from a microwave source is coupled into the oven 60 through a coaxial connector 95. The electromagnetic field propagates from left to right in the space 140 between a metallic cylindrical inner conductor 70 of the coaxial oven 60 and a metallic cylindrical outer wall 80. To prevent undesirable reflection of microwave energy out of the microwave oven 60 through the connector 95, a conical impedance matching section 85 is used to transition between the smaller-diameter coaxial connector 95 and the larger-diameter main section of the coaxial oven 60.

The outer enclosure of oven 60 including a conical impedance matching section 85 and outer wall 80 defines the boundary of a cavity which substantially prevents electromagnetic radiation from escaping from the oven 60. All of the chromatographic microwave ovens described herein comprise cavities which substantially isolate microwave electromagnetic phenomenon within the interior space defined by the boundaries of the cavity from the environment.

A cylindrical sheet of microwave absorbing material 100 is positioned concentrically about the central axis of the oven 60 in the gap between the inner and outer conductors 70 and 80. Around and adjacent to absorbing material 100 is coiled a chromatographic column 110 which is heated together with the absorbing material 100 in the oven 60. Together, the absorbing material 100 and the adjacent column 110 constitute a microwave absorbing chromatographic column assembly as taught, for example, in the Applicants' U.S. Pat. Nos. 5,939,614 and 6,029,498, and U.S. patent application Ser. No. 09/515,279, entitled "Chromatography Column For Microwave Heating", which are incorporated herein by reference. It should be understood that absorbing material 100 and the column 110 could be substituted with any microwave absorbing column assembly without materially affecting the teaching of this invention.

An optional mechanical support 120 is provided to hold the absorbing material 100 and the column 110 in place within the oven 60. As shown, the mechanical support 120 is a thin walled cylindrical structure of fixed length outside of which is wrapped the absorbing material 100 and the column 110. The mechanical support 120 need not be a cylindrical pipe nor must the absorbing material 100 and the column 110 be wrapped around it. It could just as readily be placed between absorbing material 100 and the column 110 or it could lie outside of both without materially affecting the performance of the oven 60.

Taken together, the absorbing material 100, the column 110, and the mechanical support 120 constitute a common element in all chromatographic column microwave oven embodiments described herein. Henceforth, they are treated as a single element 130 and called a column heating element. The term column heating element incorporates any microwave absorbing column assembly together with an optional mechanical support. Many different embodiments and configurations of these subcomponents are possible. It should obvious be one of average skill in the art that the invention is not limited to a specific one.

Microwave energy not absorbed by the column heating element 130 passes though a second impedance matching transition 85 and into a load element 150 which absorbs it.

All cylindrical elements within the oven 60 are concentrically oriented about the same axis. Consequently, the electromagnetic field is radially symmetric in the oven 60. The diameter of the oven 60 built in accordance with this specification is typically between 3 and 25 cm.

As specified, the oven 60 has significant drawbacks. First, the electromagnetic field strength is not constant axially in the oven 60 nor in the column heating element 130. The electromagnetic field strength decreases axially as it propagates through the oven 60 because energy is absorbed by the column heating element 130. Thus, there is a temperature gradient from high to low along the length of the column 110 in the direction of microwave propagation. The second weakness of the oven 60 is that it is energy inefficient. Much of the microwave energy 90 injected into the oven 60 is lost in the load 150. It does not heat the column heating element 130. The loss factor of the column heating element 130 can be increased so that a higher percentage of the microwave energy 90 is dissipated in the column heating element 130. However, this increases the gradient of the electromagnetic field in the axial direction making steeper the temperature profile of the column 110.

A coaxial resonant cavity chromatographic column microwave oven is far more energy efficient than the coaxial transmission line microwave oven 60. Resonant cavities are a special class of cavity as the term is used herein in which confined electromagnetic energy can develop into high field strength standing wave patterns as a result of multiple internal reflection. Virtually all microwave energy injected into a resonant cavity chromatographic column microwave oven will be absorbed by the column heating element. Coaxial resonant cavities have radially symmetric electric fields just as coaxial transmission lines do.

Figure 3:
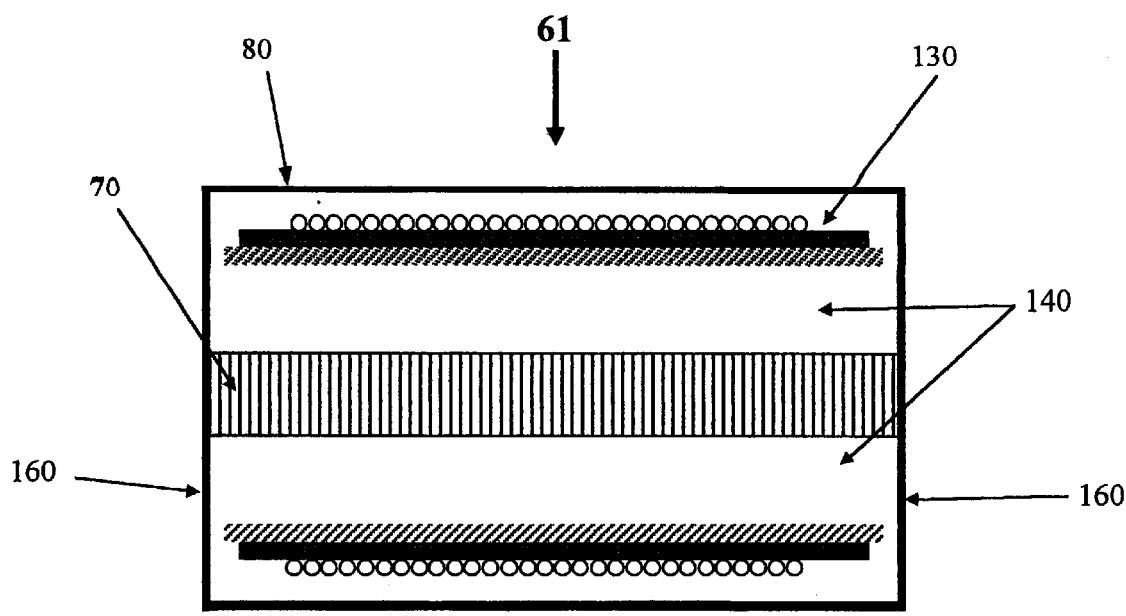
FIG. 3 is a cross-sectional view along the central axis of a chromatographic column microwave oven wherein the oven is a short-circuited coaxial resonant cavity.

FIG. 3 illustrates a chromatographic column microwave oven 61 constructed as a short circuited coaxial resonant cavity. FIG. 3 shows the cross section of the oven 61 along its central axis. The radial cross section of the oven 61 is identical to that of the oven 60 shown in FIG. 2. A metallic inner conductor 70 and a concentric metallic outer conductor 80 comprise the coaxial parts of the oven 61. They are electrically connected together at both ends with round metal discs 160 which also serve to seal the oven 61 if air in the space 140 is pumped out. A cylindrical column heating element 130 is centered around the central axis.

The internal axial length of the oven 61 is 'D'. The oven 61 will resonate at those frequencies at which the wavelength is equal to 2D, D, 2D/3, D/2, 2D/5 ... and so on. At the lowest order resonance, the cavity is one half a wavelength long. Ignoring the absorption of the field by the column heating element 130, the axial electric field strength at a fixed radius within the oven 61 is given by the following equation:

$$E(z) = E_{max} \sin(\pi z) \quad (1)$$

where:
z is the normalized axial position in the oven 61 (i.e., z=0 at one end cap 160 and z=1 at the other),
E(z) is the axial electric field strength in the oven, and
$E_{max}$ is the maximum axial electric field strength.

Figure 4:
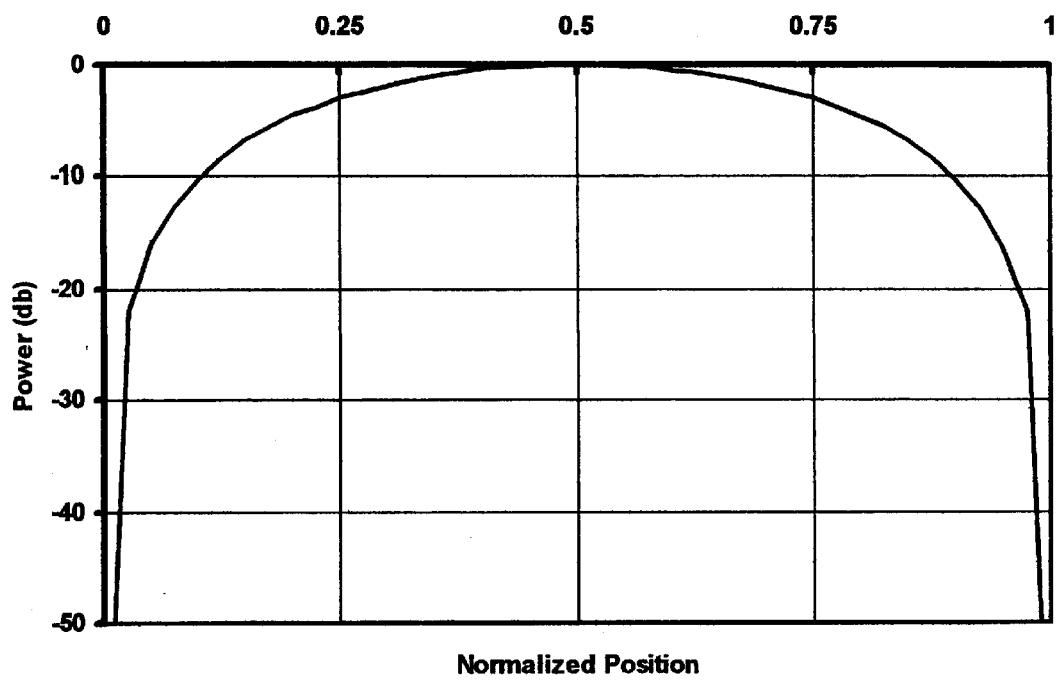
FIG. 4 is a graph showing the microwave power distribution along the length of a short-circuited coaxial resonant cavity.

The axial power distribution of the electric field is described by the following equation:

$$P = 20 \log 10[E(z)/E_{max}] \quad (2)$$

where P is the power in decibels (dB) relative to the maximum power point. FIG. 4 is a graph showing the electric field power distribution in an oven 61 along its length.

Figure 5:
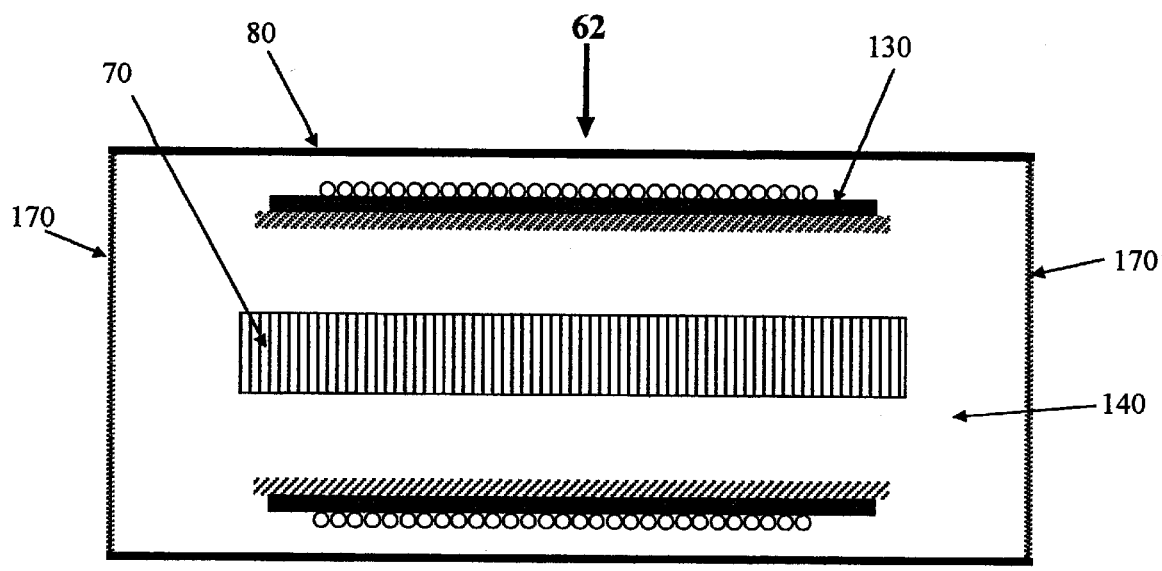
FIG. 5 is a cross-sectional view along the central axis of a chromatographic column microwave oven wherein the oven is an open-circuited coaxial resonant cavity.

FIG. 5 illustrates a similar chromatographic column microwave oven 62 constructed as an open circuited coaxial resonant cavity. FIG. 5 shows the cross section of the oven 62 along its central axis. The radial cross section of the oven 62 is identical to that of the oven 60 as shown in FIG. 2. The oven 62 has a metal cylindrical inner conductor 70, and concentric metal cylindrical outer conductor 80, between which is a concentric cylindrical oven heating element 130. The inner conductor 70 and the outer conductor 80 are not connected together electrically. The oven ends are sealed with circular endplates 170 such that the air in the space 140 inside the oven 62 can be pumped out. The endplates 170 can be metallic or nonmetallic. If metallic, then the outer conductor 80 must be longer than and not come into electrical contact with the inner conductor 70 as shown in FIG. 5.

The length of the inner conductor 70 is 'D'. The oven 62 will resonate at those frequencies at which the wavelength is equal to 2D, D, 2D/3, D/2, 2D/5 . . . and so on. At the lowest order resonance, the inner conductor 70 is one half a wavelength long. Ignoring the absorption of the field by the column heating element 130, the axial electric field strength at a fixed radius within the oven 62 is given by the following equation:

$$E(z) = E_{max} \cos(\pi z) \quad (3)$$

Figure 6:
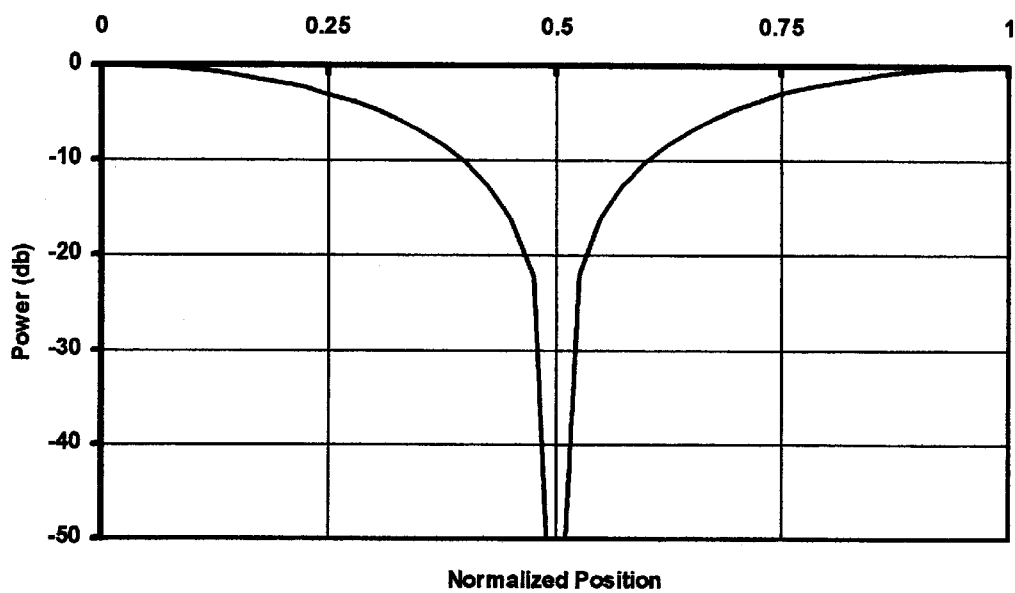
FIG. 6 is a graph showing the microwave power distribution along the length of an open-circuited coaxial resonant cavity.

FIG. 6 is a graph showing the corresponding power distribution of the oven 62 along the length of the center conductor 70.

Within the ovens 61 and 62, each single coil of the chromatographic column follows an isofield line and is thus heated isothermally. However, the axial power distributions of the electric fields in the ovens 61 and 62 respectively vary greatly as shown in FIG. 4 and 6 respectively. The power varies by 50% (about 3 dB) over the center 50% of the oven 61. The corresponding temperature gradient would also be approximately 50% as compared to ambient temperature.

There are methods with which the axial power distribution of the electromagnetic field can be altered in the ovens 61 and 62. But, the axial field strength cannot be made constant over the entire oven length. Consequently, the ovens 61 and 62 would be much longer physically than the column heating element 130. The absorption of microwave energy by the column heating element 130 in the ovens 61 and 62 will somewhat alter the power distributions shown in FIG. 4 and 6 without significantly altering the essential characteristics of these oven embodiments.

Another type of coaxial resonant cavity that could be used is a hybrid of those used the ovens 61 and 62 (i.e., a cavity with a short circuit on one side and an open circuit on the other). This cavity would resonate at frequencies where the wavelength is equal to 4D, 4D/3, 4D/5, 4D/7 . . . and so on, where D is equal to the length of the center conductor.

Circular Cylinder Resonant Cavities

Figure 7:
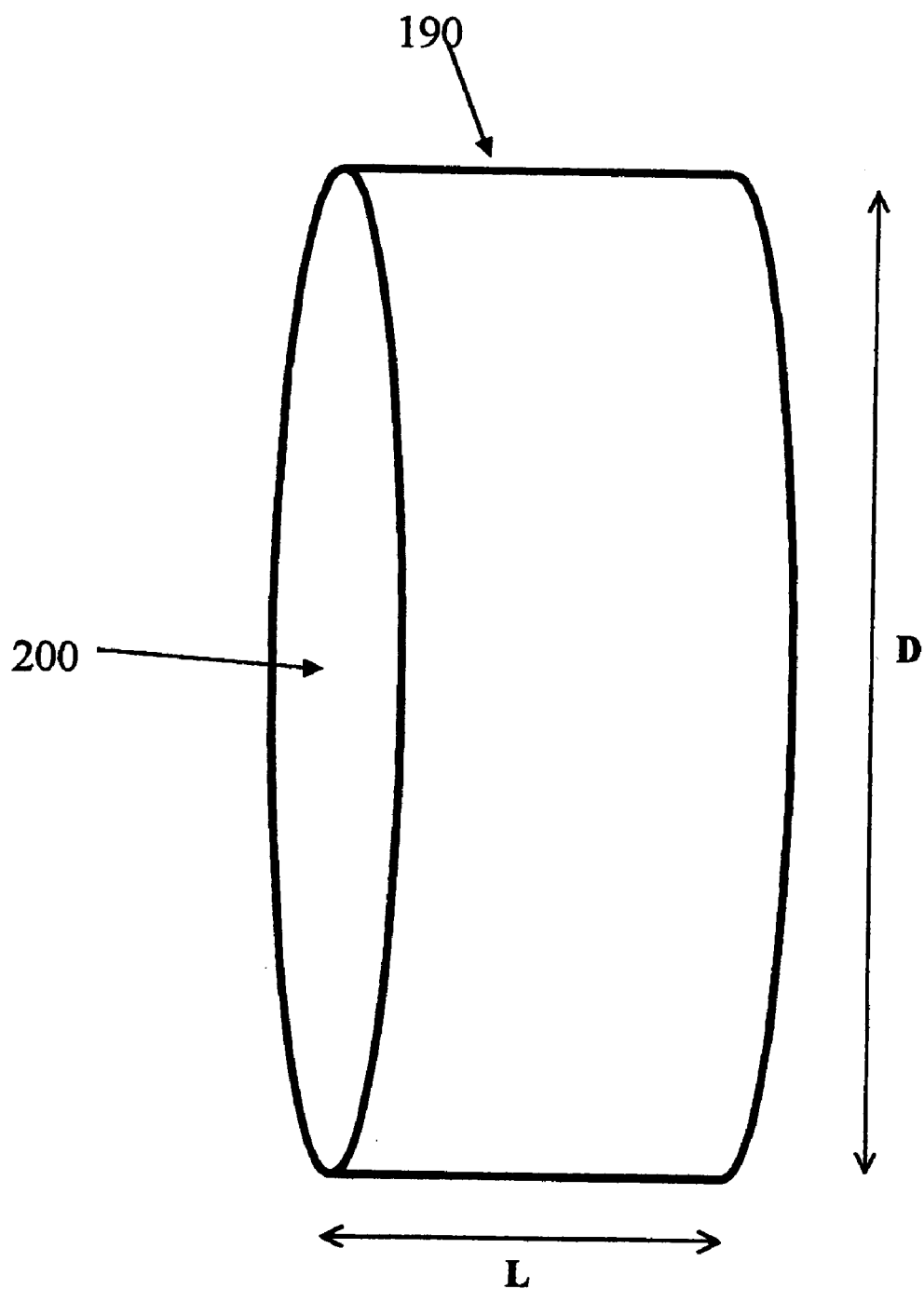
FIG. 7 is a perspective view of a cylindrical resonant cavity.

Certain modes of circular cylindrical resonant cavities have constant electromagnetic field strengths at fixed radii over their axial length and so are a better choice for a chromatographic column oven than coaxial resonator ovens. A circular cylindrical resonant cavity is essentially the same cavity shown in FIG. 3 without the center conductor. FIG. 7 is a drawing of such a resonant cavity having a diameter D and an axial length L. It consists of a metal cylinder 190 with metal end caps 200 at either end oriented perpendicular to its central axis.

Circular cylindrical resonant cavities can support many modes if the wavelength is smaller than the length or the diameter of the cavity just as a conventional rectangular microwave cavity does. Some of the possible modes are radially symmetric. Others are not. Ideally, a chromatographic column microwave oven will only support one mode so that there is no uncertainty in the electromagnetic field distribution. If more than one mode is present, the relative power distribution between the modes can change such that the field distribution varies over time. Thus, a chromatographic column microwave oven should be a substantially single mode oven and not a multi-mode oven.

The resonant frequencies for different modes in cylindrical resonant cavities can be calculated from cavity length L and diameter D. Table 1 shows the resonant frequency for various modes in three cylindrical resonant cavities, each with a diameter of 25 cm.

TABLE 1

| | Frequency (GHZ) | | |
|---|---|---|---|
| Mode | L = 8 cm | L = 15 | L = 25 cm |
| TM010 | 0.919 | 0.919 | 0.919 |
| TE111 | 2.000 | 1.219 | 0.919 |
| TM020 | 2.108 | 2.108 | 2.108 |
| TM110 | 1.463 | 1.463 | 1.463 |
| TM011 | 2.085 | 1.354 | 1.092 |
| TE211 | 2.212 | 1.542 | 1.319 |
| TE011 | 2.379 | 1.773 | 1.582 |
| TM111 | 2.379 | 1.773 | 1.582 |
| TM210 | 1.960 | 1.960 | 1.960 |
| TE311 | 2.469 | 1.892 | 1.715 |
| TM211 | 2.712 | 2.200 | 2.049 |
| TE411 | 2.762 | 2.261 | 2.115 |

The lowest order (i.e., lowest frequency) mode in each cavity is the $TM_{010}$ mode which resonates at 0.919 GHz. As the ratio between D and L decreases, the frequency spread between the $TM_{010}$ mode and the higher order modes decreases. When D/L is one, the $TM_{010}$ and $TE_{111}$ modes resonate at the same frequency and several other modes resonate at frequencies not much higher. This is a situation to be avoided. If a chromatographic column microwave oven is made with a D:L ratio of at least 2 and preferably 3, the $TM_{010}$ mode is clearly separated from the other modes such that the oven will operate as a single mode oven.

Figure 8:
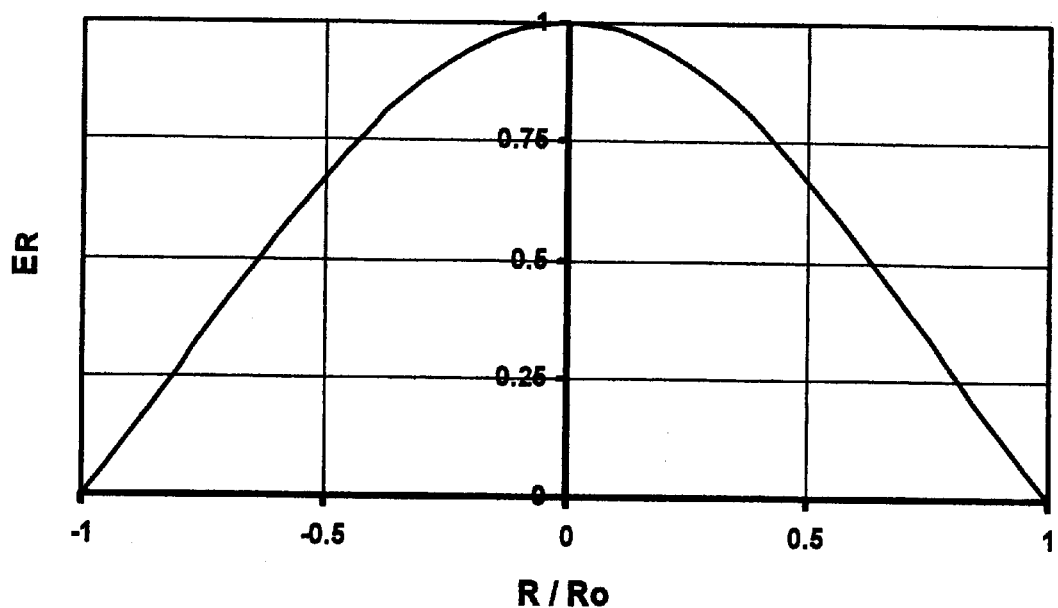
FIGS. 8 and 9 are graphs showing the radial electric field and resultant microwave power distributions respectively for the $TM_{010}$ mode in a cylindrical resonant cavity.
Figure 9:
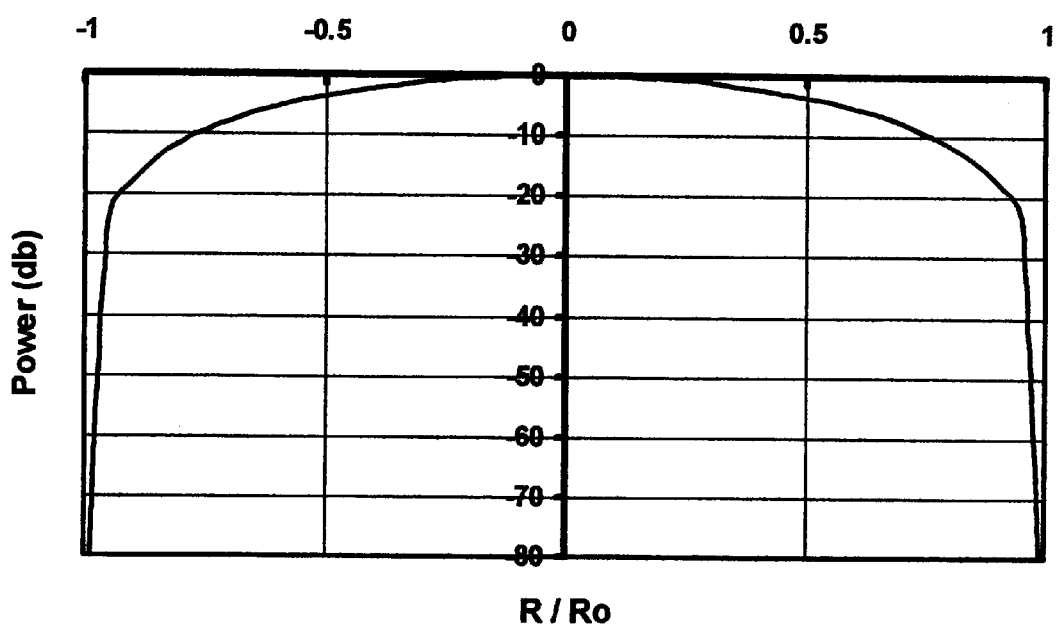

The $TM_{010}$ mode has other attractive characteristics for a column heating application. The electromagnetic field distribution is radially symmetric. More importantly, the axial field distribution is theoretically predicted to be constant over the whole length of the cavity when no perturbations are present in the cavity. All $TM_{0n0}$ modes where n=1, 2, 3, . . . share these important properties. The electric field distribution in a $TM_{010}$ resonant cavity is given by the following equation:

$$E(z) = E_{max} J_0(R/Ro) \quad (4)$$

where:
- $J_0$ is the zero$^{th}$ order Bessel function,
- R is the radius at which E(z) corresponds, and
- Ro is the radius of the resonant cavity (i.e., D/2). FIG. 8 is a graph showing the electric field distribution across the diameter of a $TM_{010}$ cavity. There is no axial variation along the length L. FIG. 9 is a graph showing the corresponding power distribution calculated by inserting Eq. 4 into Eq. 2.

A Single Mode $TM_{010}$ Chromatographic Column Microwave Oven

The $TM_{010}$ circular cylindrical resonant cavity is the most suitable structure for a chromatographic column microwave oven. It has a radially symmetric, axially invariant electromagnetic field distribution and higher order modes are readily inhibited.

Figure 10:
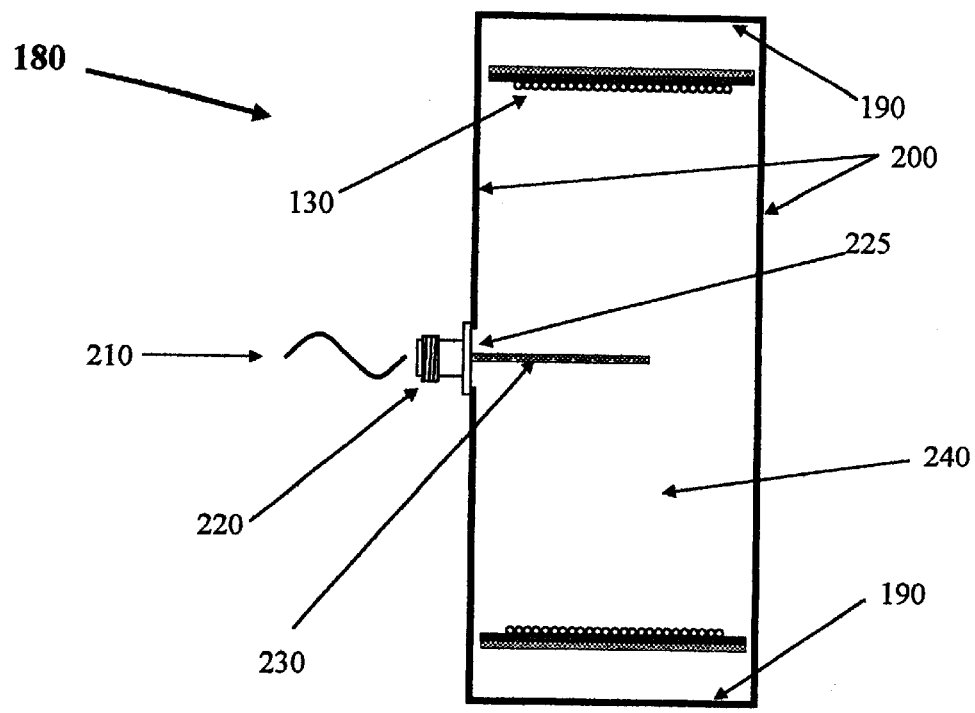
FIGS. 10 and 11 are two orthogonal cross-sectional views of a chromatographic column microwave oven wherein the oven is a cylindrical resonant cavity.
Figure 11:
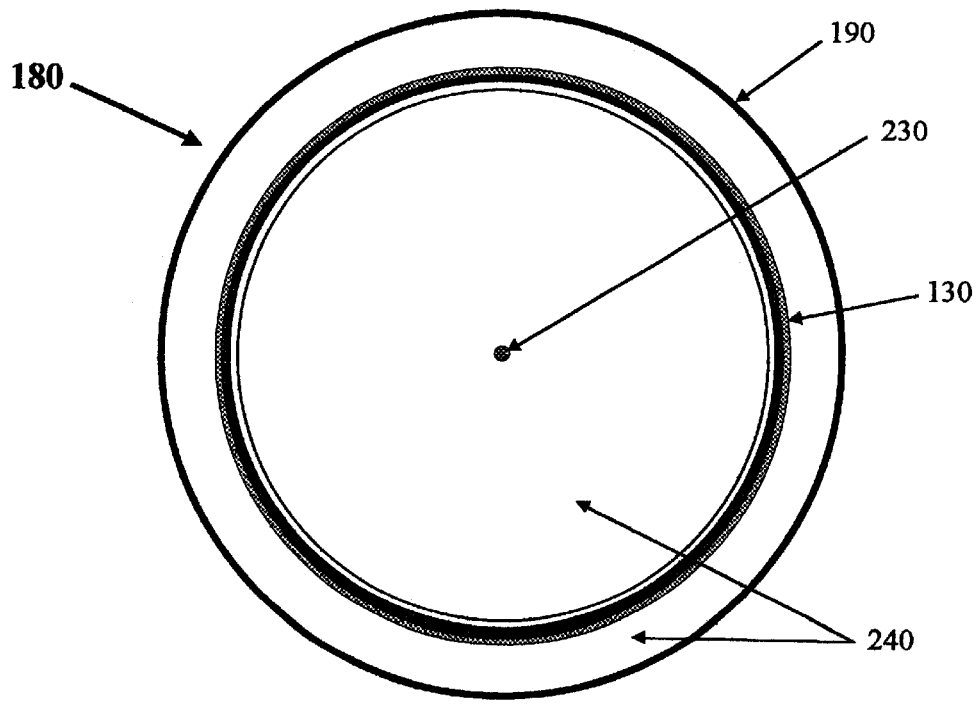

FIGS. 10 and 11 show two orthogonal cross sectional views of a chromatographic column microwave oven 180 that can utilize this mode. FIG. 10 is an axial view along the central axis and FIG. 11 a radial cross section. The oven 180 includes a circular metal cylinder 190 of length L1 and diameter D1. The cylinder 190 is closed off at either end by two circular metal caps 200 of diameter D1. Together, the cylinder 190 and the end caps 200 form the outer wall of the chromatographic column microwave oven 180 and form a circular cylindrical resonant cavity as shown in FIG. 7. To separate the $TM_{010}$ mode from higher order modes, diameter D1 should be at least twice as great as length L1.

A hole 225 is cut in the center of one of the end caps 200. A coaxial microwave connector 220 is connected to the center of the end cap 200 with the hole 225 in it. The center conductor 230 of the coaxial connector 220 protrudes into the oven 180 along the central axis through the hole 225 in the end cap 200. The center conductor 230 must not contact end cap 200.

When transmitted through the connector 220, a microwave signal 210 from a microwave source will radiate in part into the oven from the center conductor 230 which acts as an antenna. That portion of the microwave signal 210 not radiated into the oven 180 is reflected back out of the oven 180 through connector 220. Inside the oven 180 is a cylindrical column heating element 130 concentric with cylinder 190 which absorbs the microwave energy radiated into the oven 180 by antenna 230. The space 240 inside the oven 180 can be air, but much of the air can be pumped out during heating to reduce heat losses.

Compact Chromatographic Column Microwave Oven

As noted previously, chromatographic columns are very small—having internal diameters as small as 0.05 mm. All chromatographic column microwave oven embodiments described heretofore heat thin, cylindrical column heating elements which can be treated as two dimensional surfaces over which desired temperature conditions are established. These heating elements are thin because the column itself has a small diameter and because the column coil is only one or at most a few column layers in thickness. Problems associated with slow thermal conductivity in insulating materials are minimized with such column heating elements. However, even smaller microwave ovens can be constructed if the chromatographic column is bundled more tightly together or etched into a rigid substrate such as silicon.

Figure 12:
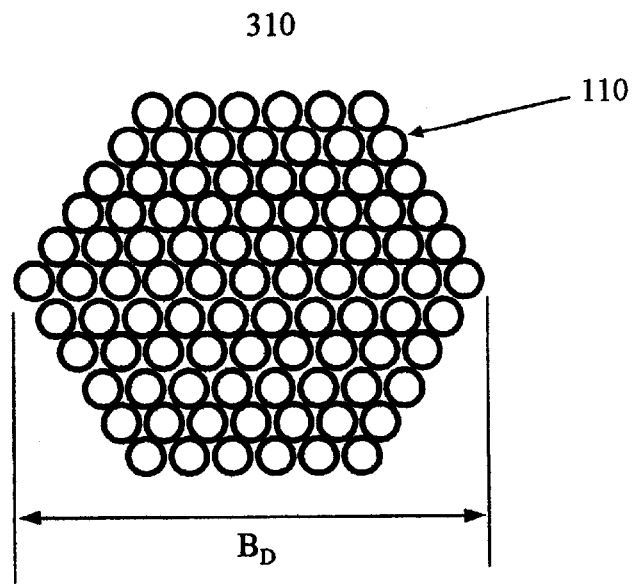
FIG. 12 is the cross-sectional view of a tightly bundled coil of chromatographic column.
Figure 13:
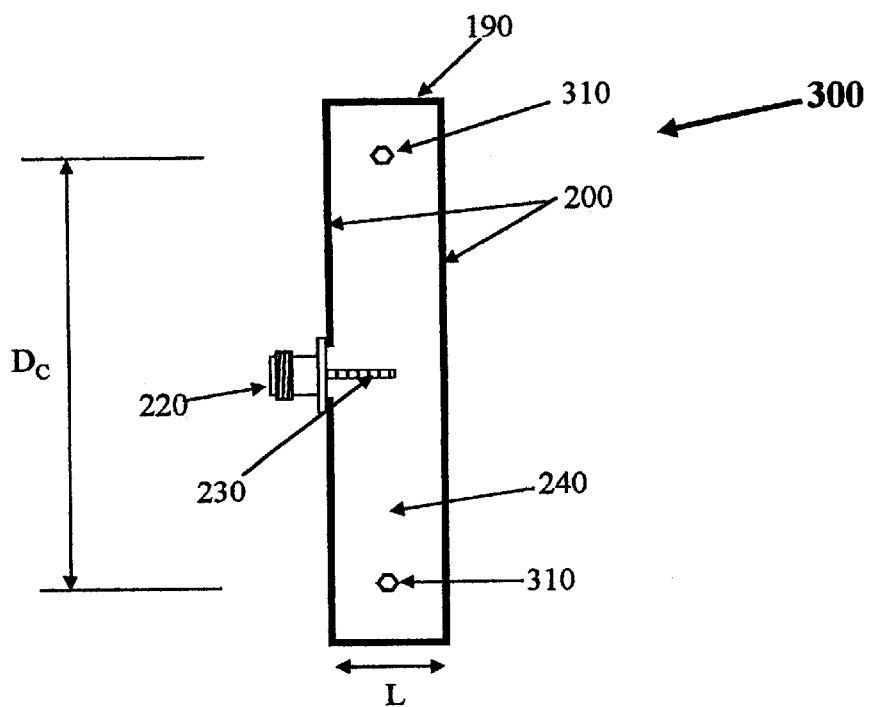
FIG. 13 is a cross-sectional view along the central axis of a compact chromatographic column microwave oven.

FIG. 12 shows the cross section of a chromatographic column 110 tightly packed into a coiled chromatographic column bundle 310 where the diameter of the column bundle 310 is denoted $B_D$. When packed in this manner, a 50 m long 0.32 mm diameter column coiled into loops 12.5 cm in diameter can be packed into a bundle for which $B_D$ is approximately 4.1 mm. FIG. 13 shows the cross section of a chromatographic column microwave oven 300 along its central axis in which a column bundle 310 having a major diameter $D_c$ is heated. The oven 300 has the same components as does the oven 180 shown in FIGS. 10 and 11 except for the substitution of the column bundle 310 for column heating element 130. The column bundle 310 must contain microwave absorbing material if it is to absorb microwave energy and be heated in the oven 300. This microwave absorbing material can be incorporated into the column 110 itself, as disclosed in the Applicants' U.S. Pat. Nos. 5,939,614 and 6,029,498, or dispersed within the column bundle 310 adjacent to the column 110.

Because $B_D$ is so small, the length L of oven 300 can be smaller than is possible with the previous oven embodiments described in this invention. The axial length of the heating section could be as small as 5 to 10 mm. In addition, the temperature profile along the length of chromatographic column 110 is not significantly affected by axial variations that might exist in the electromagnetic field within oven 300 because the axial length of the column bundle 310 is so small.

Common Elements of the Chromatographic Column Microwave Oven Embodiments

A number of chromatographic column microwave oven embodiments have been described heretofore in this invention including coaxial microwave ovens and circular cylindrical resonant cavity ovens. There are certain common characteristics of useful chromatographic column microwave ovens as taught in this invention with which controlled column temperature profiles can be achieved:

(1) Each oven is designed to substantially excite only a single resonant mode. Multiple modes and the uncertain electromagnetic field distribution that result therefrom are avoided.

(2) The cross sectional geometry of each oven about its central axis results in an electromagnetic field distribution characterized by smoothly varying, continuous isofield lines oriented about an axis which is typically collinear with the geometric central axis of the oven. A chromatographic column coiled in a column heating element which traces these isofield lines is thus exposed to an electromagnetic field strength that is constant over the length of each individual column coil. Consequently, each such coil absorbs microwave energy at substantially the same rate at all points along its length. Each single chromatographic column coil is thus an isotherm or very nearly so given the small change in axial position between adjacent coils.

Figure 14:
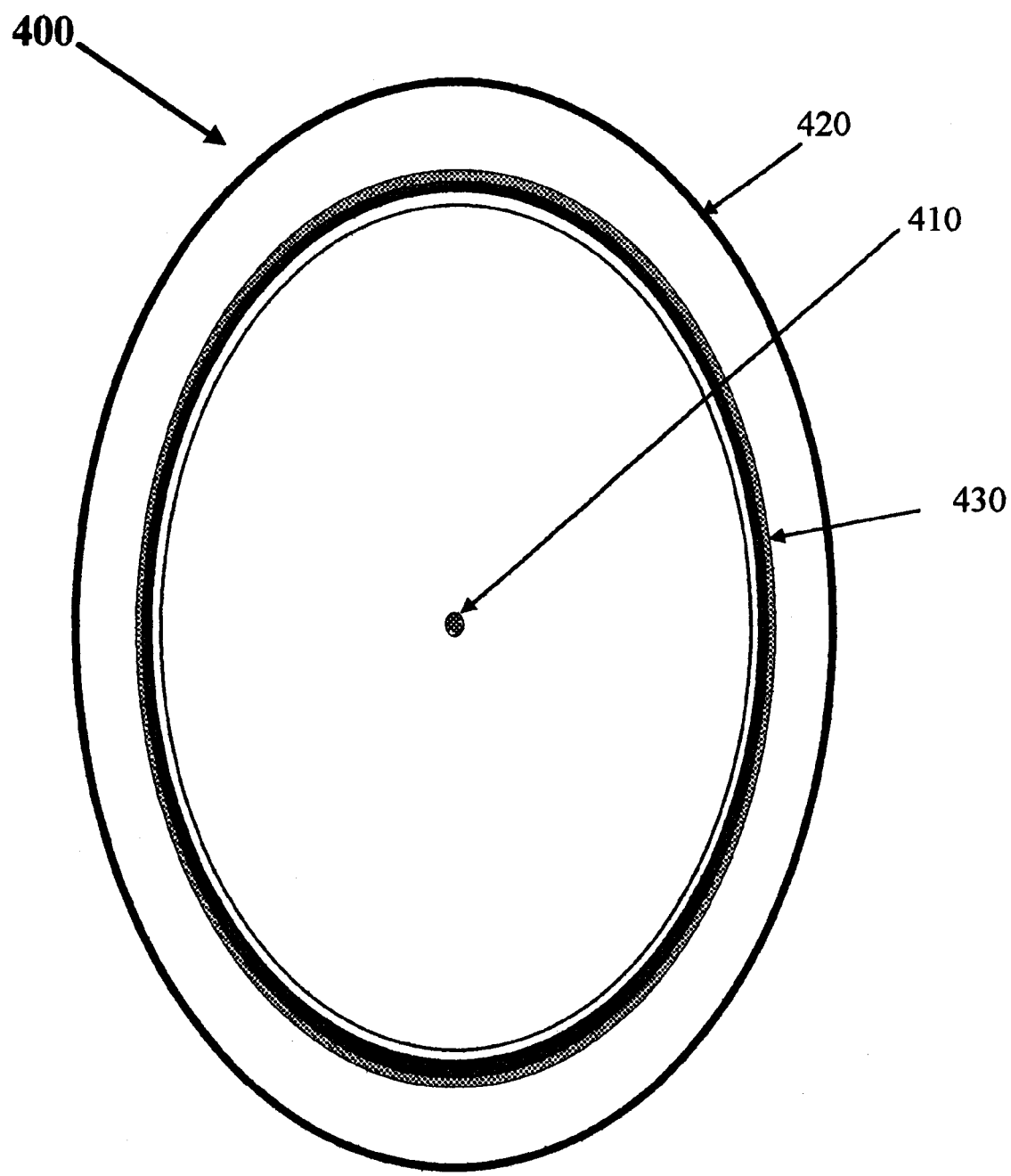
FIG. 14 is a cross-sectional view along the central axis of a chromatographic column microwave oven having an elliptical, rather than circular cross-section.

All of the chromatographic column ovens described heretofore have circular cross sections perpendicular to the central axis as have the associated column heating elements. It is certainly possible to deviate from a circular structure and still have each column coil be an isotherm. A column coil will be an isotherm if it follows an isofield line in the oven. FIG. 14 shows the cross section of an elliptical chromatographic column oven 400 perpendicular to its central axis wherein the outer metal enclosure 420 and the antenna 410 are elliptical. The electromagnetic field lines within the oven 400 will tend to follow the elliptical shape of the metal enclosure 420. The column heating element 430 is elliptical and each column coil within the heating element 430 will be an isotherm It should be understood that the present invention incorporates all chromatographic column microwave oven structures within which individual column coils closely follow isofield lines within the oven such that the temperature varies little along the length of each column coil.

(3) To achieve the desired chromatographic column temperature profile in a microwave oven, the electromagnetic field gradient from one coil of the column in the column heating element to the next must be sufficient to achieve the desired temperature difference from one coil to the next. If conditions approaching isothermal conditions are desired in the column, then the rate of microwave absorption must be substantially equal over the whole length of the column.

Transmitting Microwaves into the Oven

Figure 15:
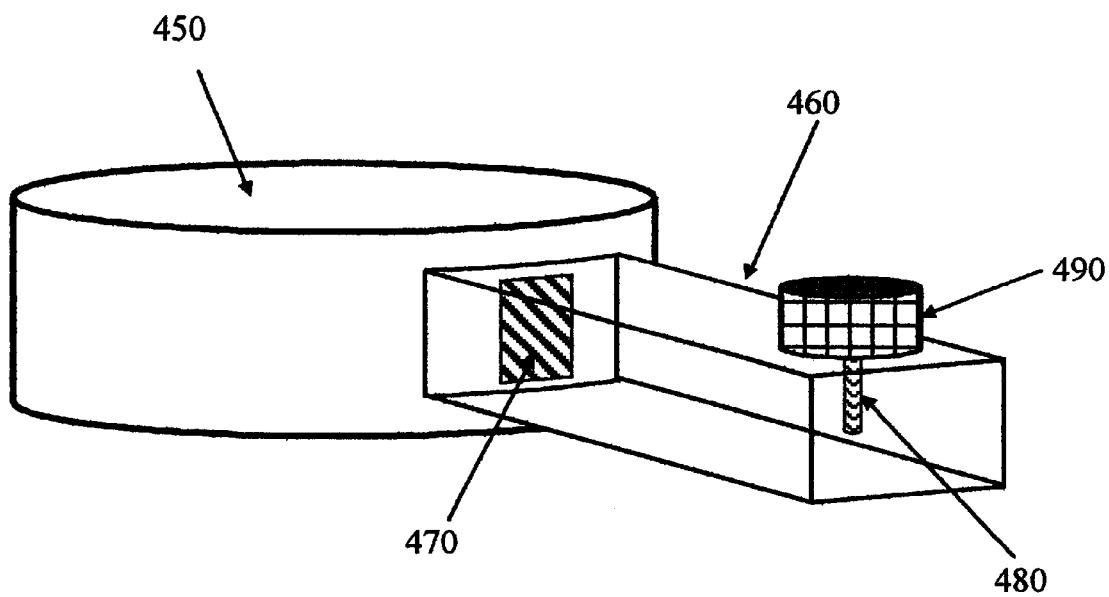
FIG. 15 shows a chromatographic column microwave oven that uses an aperture and waveguide to transmit microwave power into the oven rather than an antenna.

All chromatographic column microwave oven embodiments described in detail herein use an antenna to transmit microwave energy directly into the oven. There are other types of transmitters by which microwave energy can be transmitted into the oven. For example, an aperture can be cut in the wall of the oven through which microwave energy can be transmitted from an external waveguide apparatus into the chromatographic microwave oven. FIG. 15 shows an external view of a chromatographic column microwave oven 450 built with an aperture transmitter rather than an antenna transmitter. The oven 450 can be any of the chromatographic column microwave ovens taught herein except for the omission of the coaxial microwave connector 220 and the center conductor 230 which are shown for example in the oven 180 in FIG. 10 and the oven 300 in FIG. 13. A waveguide 460 is connected to the external wall of the oven 450. An aperture 470 is cut into the side wall of the oven 450 such that electromagnetic energy propagating down the waveguide 460 can be transmitted from the waveguide 460 into the oven 450 through the aperture 470. The aperture 470 can be an open hole or it may be a dielectric window through which electromagnetic waves can pass. Microwave energy is transmitted into the waveguide 470 via an antenna 480. Optionally, the antenna 480 can be the launcher of a magnetron microwave source 490.

Generally, any type of microwave transmitter mechanism can be used with the chromatographic column microwave ovens taught herein. The specific transmitter used to introduce microwave energy into a given oven is not a central feature of this invention.

Achieving Suitable Oven Size For a Given Operating Frequency

For most practical applications, a chromatographic column microwave oven would be operated within one of two frequency bands centered at 0.915 and 2.45 GHz respectively. These frequency bands are so called ISM bands that have been set aside for such industrial purposes as microwave heating. Thus, the resonant frequency of a chromatographic column microwave oven would typically be about 0.915 or 2.45 GHz. As shown in Table 1, an oven operating at 0.915 GHz utilizing the $TM_{010}$ mode will have a diameter of about 25 cm. If operating at 2.45 GHz, a $TM_{010}$ oven would have a diameter of about 9.3 cm. A 25 cm oven is too large to be generally practical while a 9.3 cm oven would typically be too small to accommodate a column as long as 50 m. To make a chromatographic column microwave oven that operates at a specific frequency and which has a desired size, it may be necessary to adjust its resonant frequency without adversely affecting its electromagnetic field distribution.

Figure 16:
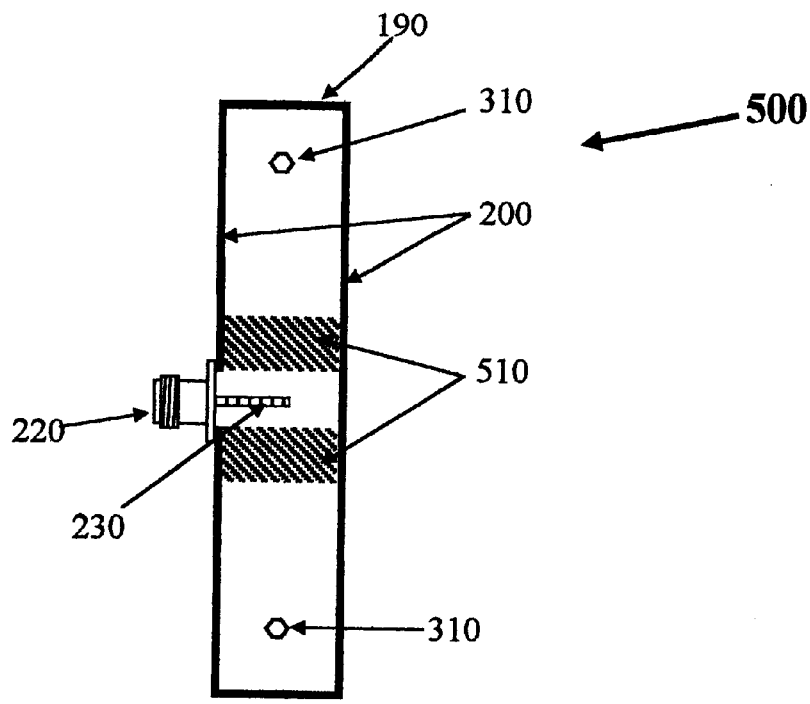
FIG. 16 is a cross-sectional view along the central axis of a chromatographic column microwave oven using a cylindrical dielectric insert to reduce the oven diameter for a given operating frequency.

One method for decreasing an oven's resonant frequency for a given diameter is to add a cylindrical dielectric element into the oven. FIG. 16 shows the cross-section of an oven 500 along its central axis that contains a cylindrical dielectric element 510. In all other respects, the oven 500 is identical to the oven 300 illustrated in FIG. 13 though it could be any oven built in accordance with the teaching of this invention. The cylindrical dielectric element 510 is placed concentrically about the center of the oven 500 so as not to disturb the radial symmetry of the electromagnetic field within the oven 500. In addition, if the cylindrical dielectric element 510 has a constant wall thickness and extends substantially along the whole axial length of the oven 500, it will not disturb the axial invariance of the electromagnetic field within the oven 500. The resonant frequency of the oven 500 can be varied by adjusting the radial thickness of the cylindrical dielectric element 510 or by adjusting its dielectric constant. The cylindrical dielectric element 510 should not absorb microwave energy appreciably or it too will be heated in the oven 500, thus compromising heating and cooling times.

Figure 17:
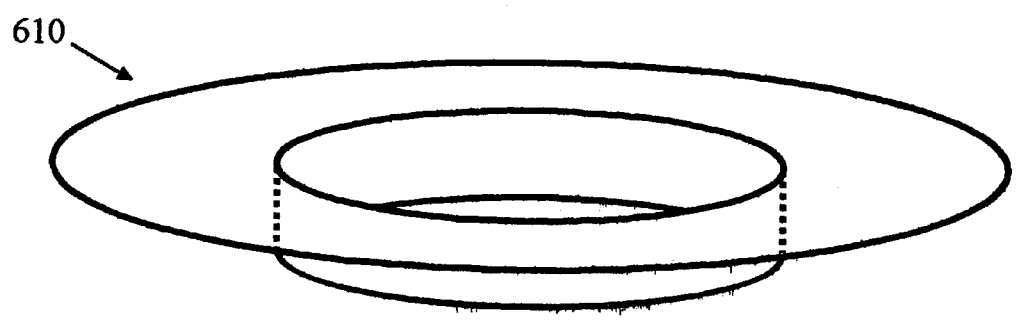
FIG. 17 shows an end cap with a raised center.

A second method for varying the diameter of a chromatographic column microwave oven for a given operating frequency is to place a radially symmetric capacitive element within the oven. One way to add such a capacitive element is to replace one or both of the end caps 200 in the oven 180 shown in FIG. 10 or the oven 300 shown in FIG. 13 with the end cap 610 shown in FIG. 17. The end cap 610 has a raised circular section at its center.

Figure 18:
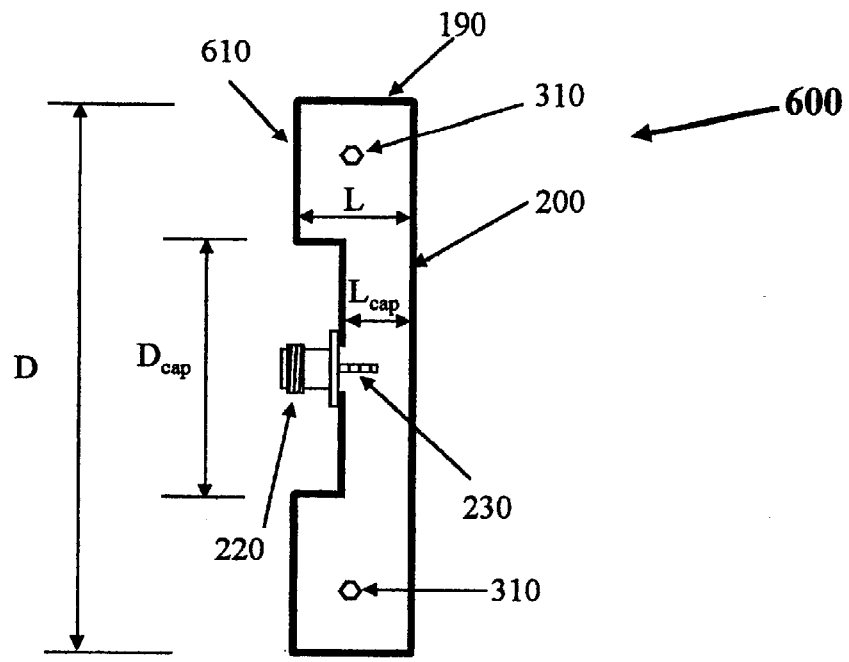
FIG. 18 is a cross-sectional view along the central axis of a chromatographic column microwave oven that uses a capacitive element to reduce the oven diameter for a given operating frequency.

FIG. 18 shows the cross section an oven 600 along its central axis which utilizes one end cap 610 and one end cap 200 in the oven 600. The oven 600 is otherwise identical to the oven 300 shown in FIG. 13 though it could be any oven built in accordance with the teaching of this invention. The raised circular section of the end cap 610 is projected into the body of the oven 600. This creates a section in the center of the oven 600 having a diameter $D_{cap}$ where the axial distance $L_{cap}$ between the end cap 610 and the end cap 200 is less than the axial distance L between the end caps 610 and 200 beyond $D_{cap}$. Where the gap between the end caps 610 and 200 is smaller, the effective capacitance between the end caps 610 and 200 is increased. The increase in capacitance results in a decrease in the resonant frequency of the oven 600 from that which would typically result from the diameter D. For a given operating frequency, the diameter of the oven 600 can be decreased below what is possible with ovens that do not utilize a capacitive element.

Figure 19:
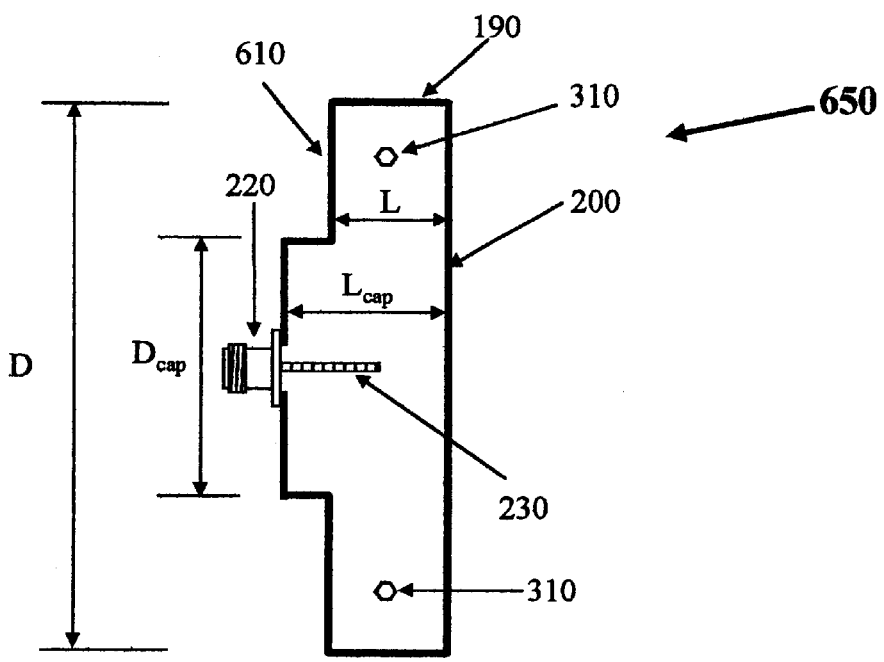
FIG. 19 is a cross-sectional view along the central axis of a chromatographic column microwave oven, which uses a capacitive element to increase the oven diameter for a given operating frequency.

A capacitive element can also be used to increase the diameter of a chromatographic column microwave oven for a given operating frequency. FIG. 19 shows the cross section of an oven 650 along its central axis that utilizes one end cap 610 and one end cap 200 in an oven 650 that is otherwise identical to the oven 300 shown in FIG. 13 though it could be any oven built in accordance with the teaching of this invention. The raised circular section of the end cap 610 is projected outward from the body of the oven 650. This creates a section in the center of the oven 650 where the axial distance $L_{cap}$ between the end cap 610 and the end cap 200 which is greater than the axial distance L between the end caps 610 and 200 beyond $D_{cap}$. The larger gap decreases the capacitance between the end cap 620 and the end cap 200 and thereby increases the resonant frequency of the oven 650 from that which would typically result from the diameter D.

The diameter of the oven 600 and the oven 650 respectively can be adjusted to more suitable values for a given operating frequency by adjusting $D_{cap}$ and $L_{cap}$ of a capacitive load. Typically $D_{cap}$ would be no greater than 65% of D. It should be understood that the capacitive element used to vary the resonant frequency of a chromatographic column microwave oven can take many forms. Any capacitive element that does not significantly disturb the radial symmetry of the electromagnetic field within an oven is suitable for this purpose. This invention incorporates all such capacitive elements used in chromatographic column microwave ovens.

A third method for achieving a desired oven size for a given operating frequency is to use a higher order resonant mode such as the $TM_{020}$ mode that has a radially symmetric electromagnetic field distribution. The nominal diameter of a cylindrical resonant cavity such as the oven 300 shown in FIG. 13 when operated at 2.45 GHz in the $TM_{020}$ mode is 21.4 cm. If a smaller diameter is needed, then a cylindrical dielectric element, a capacitive load, or both could be used. If the $TM_{020}$ mode is used in a chromatographic column microwave oven, care must be taken to inhibit lower order (i.e. lower frequency) modes with undesirable electromagnetic field distributions. The $TM_{110}$ and $TM_{210}$ modes in particular would have to be dampened as they have radially nonsymmetrical electromagnetic fields and always have lower resonant frequencies than does the $TM_{020}$ mode. When undesirable lower order resonant modes are inhibited, a $TM_{020}$ mode oven will substantially operate as a single mode oven just as a $TM_{010}$ mode oven does.

Minimizing Power Consumption

The total power required to operate a chromatographic column microwave oven is directly related to the total microwave power that must be generated to heat the column heating element. Of the total microwave power generated, some portion is transmitted into the oven and some portion is reflected by the oven back into the microwave source where it is lost as useless heat. The microwave power transmitted into the oven is either absorbed in the column heating element or dissipated in the form of heat in walls of the oven Finally, microwave power that is absorbed in the column heating element is converted into heat energy that either increases the temperature of the column heating element or is dissipated away and lost to its environment. Thus, minimizing the power consumption of a chromatographic column microwave oven entails: (A) minimizing thermal losses in the column heating element; (B) minimizing microwave loses in the walls of the oven; and (C) minimizing the reflection of microwave power by the oven.

A) Minimizing Thermal Losses in the Column Heating Element. The total amount of thermal energy that a chromatographic column oven needs to supply to a column heating element to attain a desired temperature is described by the following equation:

$$P_{TOT} = \Sigma M_i C_{pi} \Delta T/t + + P_{COND} + P_{RAD} \quad (5)$$

where $P_{TOT}$ is the total thermal power input into the column heating element, $M_i$ is the mass of each part 'i' in the column heating element, $C_{pi}$ is the specific heat of each part 'i', $\Delta T/t$ is the target rate of temperature increase per unit time, $P_{COND}$ is the heat transferred from the column heating element to other parts of the oven and to the environment by direct thermal conduction mechanisms.

$P_{RAD}$ is the heat transferred from the column heating element to other parts of the oven and to the environment by radiative processes.

As is clear from Eq. (5), the energy requirements can be minimized by: (1) minimizing the mass of the column heating element and (2) minimizing the thermal energy losses from the column heating element via conduction and radiation. Direct microwave heating of an appropriately designed column heating element makes it possible to reduce the mass of the material to be heated to little more than that of a standard chromatographic column. This is one of the key advantages of heating chromatographic columns with microwave energy as compared to alternative heating methods.

The thermal losses associated with conduction to the air and with radiation increase in direct proportion to the surface area of the column heating element that is exposed to the environment. Thus, minimizing the surface area of the column heating element is an effective way to reduce thermal losses via conduction to the air in the oven and via radiation. The surface area of the heating element is most easily reduced by wrapping the chromatographic column into a tight bundle as illustrated in FIG. 12 and utilized in the oven 300 shown in FIG. 13.

Thermal losses via conduction to the air in the oven can also be reduced by removing some of the air. Even a modest vacuum of 75 Torr will reduce these conduction losses by 90%.

A column heating element will also lose heat via conduction to the mechanical support assembly that holds the column heating element within the oven. To reduce this heat loss, the mechanical support should have minimal thermal mass so as that it will not hold any more thermal energy than is necessary. It should be constructed from materials which can withstand exposure to high temperature, have low thermal conductivity, do not absorb microwave energy appreciably, and which will not disturb the electromagnetic field distribution within the microwave oven. Appropriate materials include many ceramics such as aluminum oxide and high temperature plastics such a polyimide. In addition, the cross sectional area of the mechanical supports which physically connect the heated portion of the column heating element to the oven walls should be reduced as much as is practical to minimize the flow path through which thermal energy can conduct to the oven walls.

Radiative losses from a column heating element will typically be the largest source of thermal loss. Radiative losses are directly proportional to the emissivity of the material on the surface of the heating element. Reducing the emissivity of the heating element is not very practical, however.

Emissivity is a unitless coefficient having a value between 0 and 1. It represents how much a given material radiates or absorbs at a given temperature as compared to a perfect black body which has an emissivity value of 1. Electrically non-conducting materials such as plastic and ceramic typically have emissivity values of 0.9 or greater. As these materials are the most suitable for usage in a column heating element in chromatographic column microwave ovens, it is not practical to significantly reduce direct radiative losses of a column heating element by using materials with low emissivity values. However, radiative losses can be reduced indirectly.

Most radiation emitted from a hot column heating element will strike the interior surface of the metal walls of the microwave oven. Most metals have emissivity values less than 0.2 and so are good reflectors of this radiation because the reflection coefficient for different materials is related to (1—emissivity). Consequently, most of the thermal energy radiated by a column heating element which strikes the metal walls of the oven is not absorbed by the walls but is reflected back into the oven. Thus, if the emissivity of the interior surface of the oven walls is minimized, then much of energy radiated by the heating element will be internally reflected in the oven until it strikes a surface with a high emissivity value where it will be absorbed. The column heating element is one of the few parts inside the oven with a high emissivity value. Thus, most thermal radiation emitted by the column heating element will find its way back to the column heating element.

The emissivity of the interior walls of the oven can be minimized by: (1) using a material with a low emissivity value such as aluminum, gold, copper or silver; and (2) by polishing the walls to reduce surface roughness. A well polished gold surface has an emissivity value of less than 0.02. The entire wall need not be made of a precious metal such as gold to achieve the desired effect. A thickness on the order of 250 nm is sufficient.

B) Minimizing Microwave Losses in the Walls of the Oven. When microwave energy is transmitted into a chromatographic column microwave oven, it induces electrical currents to flow in the interior walls of the oven. Because of resistive losses in the walls, some of the microwave energy is dissipated in the form of heat. The resistive loses are inversely proportional to the conductivity of the material in which the electrical currents flow. Thus, using high conductivity metals such as copper, aluminum, or gold on the interior of the oven minimizes unwanted microwave losses in the walls.

It may be necessary to open any useful chromatographic column microwave oven so that chromatographic columns can be changed. Consequently, there is a potential for resistive losses in the seams that will exist between the different parts that comprise the walls of the oven. Care must be taken in the design of the oven to ensure reliable, high conductivity connections between these different parts so as to reduce associated microwave wall losses.

C) Minimizing the Reflection of Microwave Power by the Oven. If the output impedance of the microwave source used to generate microwave power and the input impedance of the oven to which it is attached do not match, then much of the power transmitted to the oven will be reflected back to the microwave source and lost. To minimize microwave reflection and thereby reduce system power consumption, microwave source and oven impedances respectively should be matched as well as possible.

One aspect of matching source and oven impedances is making sure that the frequency of the microwave signal from the source substantially matches the resonant frequency of the oven. If the output frequency of the microwave source can be changed electronically, then it is a simple matter to adjust the frequency to minimize reflection. On the other hand, if the microwave source is something like a magnetron that has a fixed output frequency, then the resonant frequency of the oven may need to be adjusted to match the source frequency. Tuning the oven frequency requires the usage of a mechanical tuning element. FIG. 20 shows a chromatographic column microwave oven system 700 that has an adjustable resonant frequency. The oven system 700 includes an oven 300 identical to that shown in FIG. 13 though it could be any oven built in accordance with the teaching of this invention. To the oven 300 has been added the frequency tuning element 710. The frequency tuning element 710 is any device capable of changing the resonant frequency of the oven 300 including, for example, a retractable pin protruding into the oven 300. Adjusting the length $L_{tun}$ of the frequency tuning element 710 changes the resonant frequency of the oven 300. If it is necessary to dynamically control the resonant frequency of the oven 300 using an electronic signal from an electronic controller, then an optional electromechanical interface 720 can be added to the oven system 720. The electromechanical interface 720 could be a stepper motor.

Even when the microwave source frequency substantially matches the resonant frequency of a chromatographic column microwave oven, the impedance match between the source and the oven may still be poor resulting in excessive reflection of microwave power. In these circumstances, additional impedance matching is needed.

The easiest way to adjust the input impedance of a chromatographic column microwave oven is to adjust the length of the antenna. In practice, changing the length of the center conductor 230 also changes the resonant frequency of the oven 300. Referring to FIG. 13, adjusting the length of the center conductor 230 which acts as the antenna will adjust the input impedance of the oven 300. The optimal length varies with the total loss factor of the oven 300 that primarily depends in turn upon the loss factor of the column bundle 310. In some circumstance, the loss factor of a chromatographic column microwave oven is not expected to change; i.e. only a single column heating element will be used in an oven or the total column length used in column heating elements does not change. In these circumstances, optimizing the length of the center conductor/antenna in an oven may be all that is required to achieve a very good impedance match to a microwave source and thereby substantially eliminate the reflection of microwave power from the oven. If a waveguide is used instead of an antenna to transmit microwave energy into a chromatographic column microwave oven as shown in FIG. 15, then the dimensions of the coupling aperture can be adjusted to achieve a good impedance match between the microwave source and the oven.

When a suitable impedance match cannot be achieved by optimizing antenna length or by optimizing the coupling aperture dimensions, more sophisticated impedance matching techniques must be used. One useful impedance matching method utilizes so called stub tuners. A stub tuner is a device that places one or more stubs in parallel with an electrical load. Stubs consist primarily of a length transmission line terminated by an electrical short or open circuit. The length of the transmission line may be adjustable. The stub(s) change the input impedance seen by a microwave source attached to the stub tuner/load combination. By adjusting the length of the transmission lines in the stubs, the input impedance seen by a microwave source can be adjusted until a good match is achieved to the load. Microwave losses are very low in a well designed stub tuner. Thus, a stub tuner can be used to achieve an impedance match between a microwave source and a load without appreciable loss of microwave energy.

FIG. 21a shows an electrical diagram of stub tuner 800 which can be used to connect a microwave source 810 to a chromatographic column microwave oven 820. The stub tuner 800 includes a through line 830 that transmits microwave signals from the input of the stub tuner to the output. One or more stubs 840 are connected to the through line 830 at various positions along its length. The stubs 840 includes a length $L_{stub}$ of transmission line terminated by an electrical short circuit or an open circuit. The stub tuner 800 can be adjusted by changing $L_{stub}$ of at least one of the stubs 840. The stub tuner depicted electrically in FIG. 21a can be implemented using coaxial line, microstrip, or waveguide transmission lines and shorts.

FIG. 21b shows a stub tuner 800 that can be used for impedance matching with any chromatographic column microwave oven which uses a coaxial transmission line to transmit microwave power to the oven. The stub tuner 800 includes a metal enclosure 850 containing a circuit board 870. Coaxial connectors 860 and 861 are used to feed microwave power into and out of the stub tuner 800. The circuit board 870 includes through line 830 that connects the coaxial connectors 860 and 861 and one or more fixed length stubs 840. If the stub tuner 800 is to be adjustable, the circuit board 870 includes a connection line 880 connected to a variable stub 845. The stub tuner 800 can be adjusted by changing the length of the variable stub 845. The variable stub 845 could be discrete lengths of terminated coaxial transmission line that a user swaps out as necessary to match source and oven impedances. Optionally, the variable stub 845 could include a transmission line with a sliding element such as a telescoping coaxial line. If a variable short 845 with a sliding element is used, it can be connected to an electromechanical interface 890 such as a stepper motor such that an electronic controller could be used to automatically and dynamically adjust the variable stub 845 and so optimize the impedance match between a microwave source and an oven.

Many different impedance matching methods can be used to reduce microwave reflection from chromatographic column microwave ovens and thereby reduce power consumption. Several specific techniques and apparatuses have been described herein. However, it should be understood that the present invention generically incorporates any device or method for matching the impedance of a chromatographic column microwave oven to a microwave source and thereby increase microwave efficiency and reduce system power consumption.

When properly tuned so that the microwave source frequency substantially equals the resonant frequency of the oven and the source and oven impedances are matched, the system can be over 99% efficient in transmitting available microwave energy into the oven. If oven losses are minimized, then over 95% of this energy can in turn be transferred directly into a column heating element in the form of heat.

Measuring the Temperature in the Oven

Measuring the temperature of a column in a chromatographic column microwave oven is more difficult than measuring the temperature of a conventional chromatographic oven. Most temperature measurement methods use: (1) a temperature sensor that is placed where it will reach thermal equilibrium with an object to be measured and (2) metal wires to transmit information from the sensor to some remote electronics for processing. Such a configuration is problematic in a microwave oven because the metal wires can disturb the electromagnetic field within the oven and because they can act as undesirable antennas which transmit microwave radiation out of the oven. Such problems can be minimized if the signal lines from the temperature sensor run perpendicular to the electric field lines within the microwave oven. Metal wires perpendicular to the electromagnetic field lines in a microwave oven are essentially invisible to the electromagnetic field in the microwave oven. They do not disturb the field nor do they draw energy from it.

Figure 22:
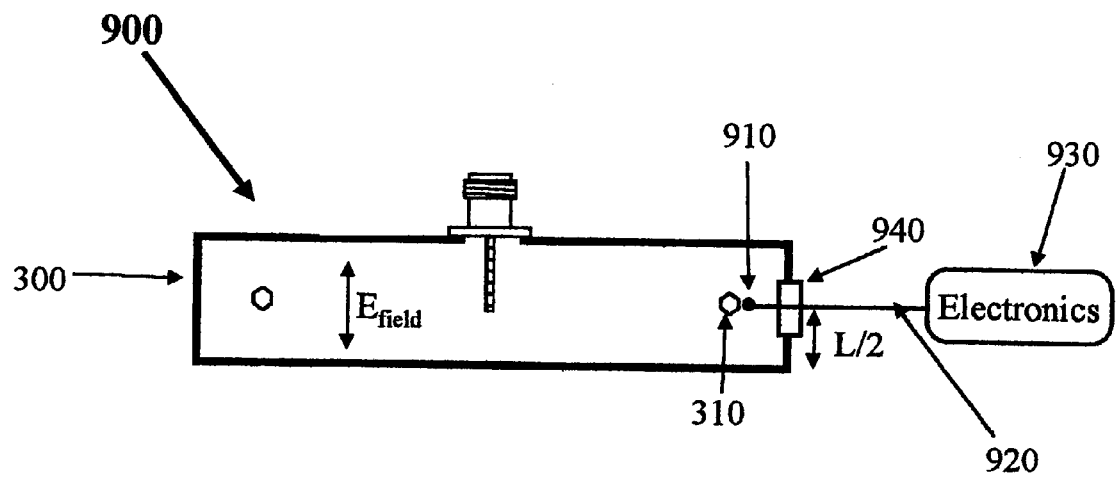
FIG. 22 shows a chromatographic column microwave oven system that utilizes a temperature sensor placed in thermal contact with the column heating assembly.

FIG. 22 shows a system 900 that utilizes a temperature sensor to measure the temperature of a chromatographic column. The system 900 includes an oven 300 which is identical to the oven 300 shown in FIG. 13 though it could be any oven built in accordance with the teaching of this invention. A temperature sensor 910 is placed in contact with or in proximity to the column bundle 310 such that it is in thermal equilibrium with the column bundle 310. The temperature sensor 910 is any temperature measurement device such as a thermocouple, RTD, or thermistor for which proper operation requires that the measurement element be at or near the same temperature as the object to be measured. One or more signal wires 920 transmit the signal from the temperature sensor 910 to the external electronics 930 for signal processing. The electric field lines run in the axial direction in the oven 300 as shown in FIG. 22. The signal wires 920 should extend within the oven 300 in a direction that is substantially perpendicular to the axial central axis of the oven 300 so as to be perpendicular to the electric field lines. Preferably, the signal lines 860 should be placed approximately halfway between the end caps 200 or at point L/2 along the cylinder 190 that forms the side wall of oven 190. Optionally, a feedthrough connector 940 could be used to get the signal lines through the cylinder 190. Preferably, the feedthrough connector 940 should be airtight and it should prevent the leakage of any microwave energy out of the oven 300 by the signal lines 920.

An alternative temperature measurement means is a non-contact, infrared temperature measurement device. An infrared temperature sensor measures the temperature of objects by analyzing the infrared radiation they give off. Such a measurement can be made remotely. Remote measurement is advantageous for a chromatographic column microwave oven because the temperature measurement means will not disturb the operation of the oven. Another advantage of infrared temperature measurement devices is that they have a faster response time than do temperature measurement means for which the temperature sensor must be in thermal equilibrium to make a measurement. A faster response time makes it easier to accurately control the temperature of a column heating element during fast temperature ramps.

Figure 23:
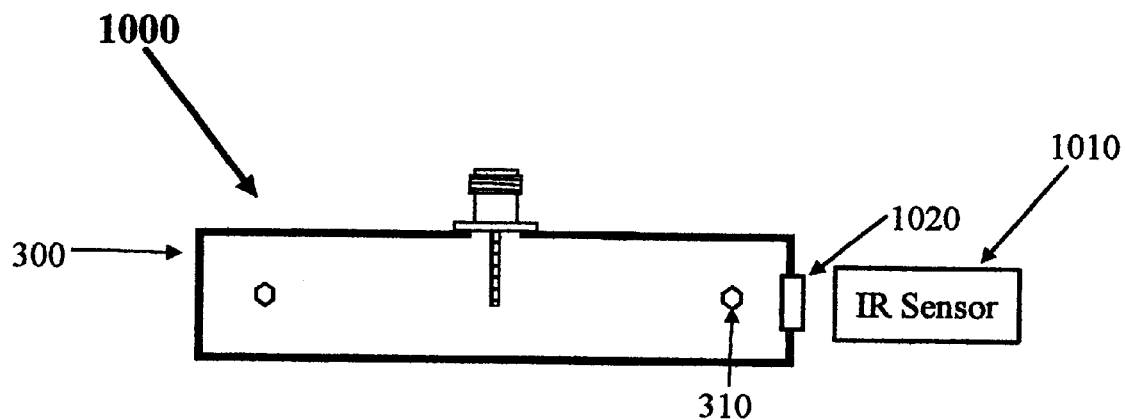
FIG. 23 shows a chromatographic column microwave oven system that utilizes an infrared temperature sensor placed outside the oven to measure the temperature of the column heating element.

FIG. 23 shows a system 1000 that utilizes an infrared temperature sensor to measure the temperature of a chromatographic column. The system 1000 includes an oven 300 that is identical to the oven 300 shown in FIG. 13 though it could be any oven built in accordance with the teaching of this invention. An infrared temperature sensor 1010 is placed outside the oven 300. It is exposed to the infrared radiation given off by the column bundle 310 through an infrared transparent window 1020 placed in the cylinder 190 which forms the side wall of the oven 300. Alternatively, the window could also be placed in one of the end caps 200.

Controlling the Microwave Source Used to Drive the Oven

Figure 24:
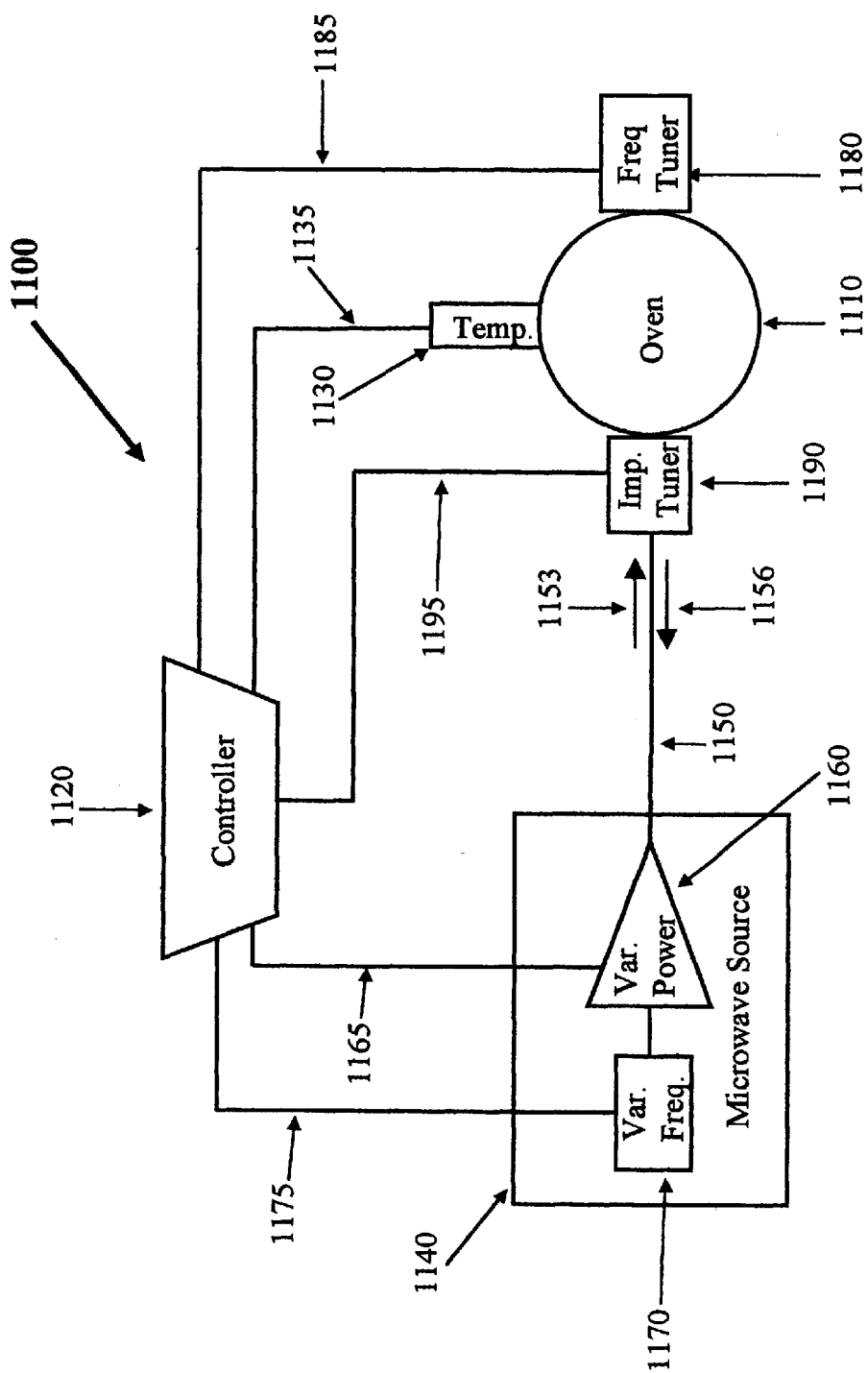
FIG. 24 shows a system which can control the temperature of a column in a chromatographic column microwave oven and which can control the efficiency of the microwave power source utilizing indirect measurement of the power level of the microwave signal reflected by the oven.

A chromatograph that includes a chromatographic column microwave oven must continuously control the temperature of the column heating element in the oven in order to generate useful temperature ramps. Continuous oven temperature control is achieved via control of the microwave source used to generate the microwave signal that is transmitted into the oven. FIG. 24 shows a system 1100 capable of: (1) controlling how much microwave power is transmitted to a chromatographic column microwave oven and (2) controlling the power efficiency of the microwave source. The main components of system 1100 are a microwave oven 1110 built in accordance with the teaching of this invention, a controller 1120, a temperature sensor 1130, and a microwave source 1140. The oven 1110 is any microwave oven used to heat a chromatographic column. The controller 1120 is understood to be any electronic system or computer capable of receiving input signals and generating output signals in response to the inputs in accordance with preprogrammed instructions. The temperature sensor 1130 is any temperature measurement apparatus with which the temperature of the chromatographic column within oven 1110 can be determined such as the temperature sensors shown in FIG. 22 and FIG. 23. The microwave source 1140 is any microwave signal generator capable of producing enough microwave power to heat a chromatographic column in oven 1110. For the purposes of this description, the microwave source 1140 includes all components used to generate, amplify, attenuate, modulate, monitor, or otherwise alter the microwave signal transmitted to the oven 1110.

The microwave source 1140 generates and transmits a microwave signal 1153 to the oven 1110 via a transmission line 1150. The temperature sensor 1130 measures the temperature of the chromatographic column within the oven 1110 and transmits a corresponding signal to the controller 1120 via the signal line 1135. If the temperature is too high or too low, the controller 1120 adjusts the variable power element 1160 within the microwave source 1140 via control line 1165 and thereby changes the power level of the microwave signal 1153 being transmitted to the oven 1110. The variable power element 1160 is any component by which the output power of the microwave source 1140 can be adjusted, including but not limited to variable gain amplifiers, variable attenuators, and circuits which essentially turn the microwave power on and off such that the total microwave output power is modulated by controlling the duty cycle. Together, the controller 1120, the temperature sensor 1130, and the variable power element 1140 comprise a closed temperature control loop.

Unless the oven 1110 and microwave source 1140 are tuned, much of the microwave signal 1153 generated and transmitted by the microwave source 1140 can be reflected by the oven 1110 back to the microwave source 1140 where it is dissipated as useless heat. Various optional elements can be added to the system 1100 to improve overall efficiency.

The proportion of the microwave power reflected by the oven 1110 is determined by how close the input impedance of the oven 1110 matches the output impedance of the microwave source 1140. The impedance match is significantly affected by the how closely the microwave frequency generated by the microwave source 1140 matches the resonant frequency of the oven 1110—the closer the respective frequencies, the less microwave energy is reflected by the oven 1110. Matching the output frequency of the microwave source 1140 to the resonant frequency of oven 1110 can be achieved by varying either the frequency of the microwave source 1140 or the resonant frequency of oven 1110.

If the frequency of the microwave source 1140 can be varied, then the controller 1120 is connected to the variable frequency element 1170 within the microwave source 1140 by control line 1175. The variable frequency element 1170 is any component by which the frequency of the microwave source 1140 can be varied including voltage controlled oscillators and mechanical tuning elements. The controller 1120 fixes the power level of microwave signal 1153 at a constant value by outputting a constant signal on control line 1165 connected to variable power element 1160. The controller 1120 then varies the frequency of the microwave signal 1153 by adjusting the variable frequency element 1170 via the control line 1175 until the temperature measured with the temperature sensor 1130 is maximized, thereby indicating that the output frequency of the microwave source 1140 essentially matches the resonant frequency of the oven 1110 and the reflected microwave signal 1156 is minimized.

If microwave source 1140 does not have an adjustable frequency, then the resonant frequency of oven 1110 may need to be varied. Magnetron sources, for example, do not typically have adjustable output frequencies. In order to vary the resonant frequency of the oven 1110, the controller 1120 is connected to an optional frequency tuning element 1180 on the oven 1110 by control line 1185. The frequency tuning element 1180 is any component by which the frequency of the microwave source 1180 can be varied such as the frequency tuning element 710 combined with the electro-mechanical interface 720 shown in FIG. 20. The controller 1120 fixes the power level of microwave signal 1153 at a constant value by outputting a constant signal on control line 1165 connected to variable power element 1160. The controller 1120 then varies the resonant frequency of the oven 1110 by adjusting the frequency tuning element 1180 via the control line 1185 until the temperature measured with the temperature sensor 1130 is maximized.

As described previously, additional impedance matching may be necessary to further reduce reflected power to optimal levels. If so, an optional impedance matching element 1190 is added to the system 1100. The impedance tuning element 1190 is any component by which the input impedance of the oven 1110 can be varied such as the stub tuner 800 shown in FIG. 21b. In order to vary the input impedance of the oven 1110, the controller 1120 is connected to the optional impedance tuning element 1190 by control line 1195. The controller 1120 fixes the power level of microwave signal 1153 at a constant value by outputting a constant signal on control line 1165 connected to variable power element 1160. The controller 1120 then adjusts the impedance tuning element 1190 via the control line 1195 until the temperature measured with the temperature sensor 1130 is maximized.

The procedures described for using system 1100 to adjust either the output frequency of the microwave source 1140, the resonant frequency of the oven 1110, or the input impedance of the oven 1110 require that the microwave signal 1153 be kept essentially constant. They also require the usage of the temperature sensor 1130 to indirectly measure how much power is being lost in the reflected microwave signal 1156. This procedure interferes with the normal control loop used to control the temperature of the column within the oven 1110. Consequently, the system 1100 is not well suited for simultaneously optimizing the impedance match in the system and controlling the column temperature. This is not a significant limitation however because the oven resonant frequency and input impedance do not change significantly except perhaps when a major event occurs such as the column bundle in the oven is changed. Thus, the system 1100 can adjust frequencies or impedances immediately after significant events if necessary, then hold constant the frequencies and impedances while the column temperature control loop is utilized for standard column heating operations.

Figure 25:
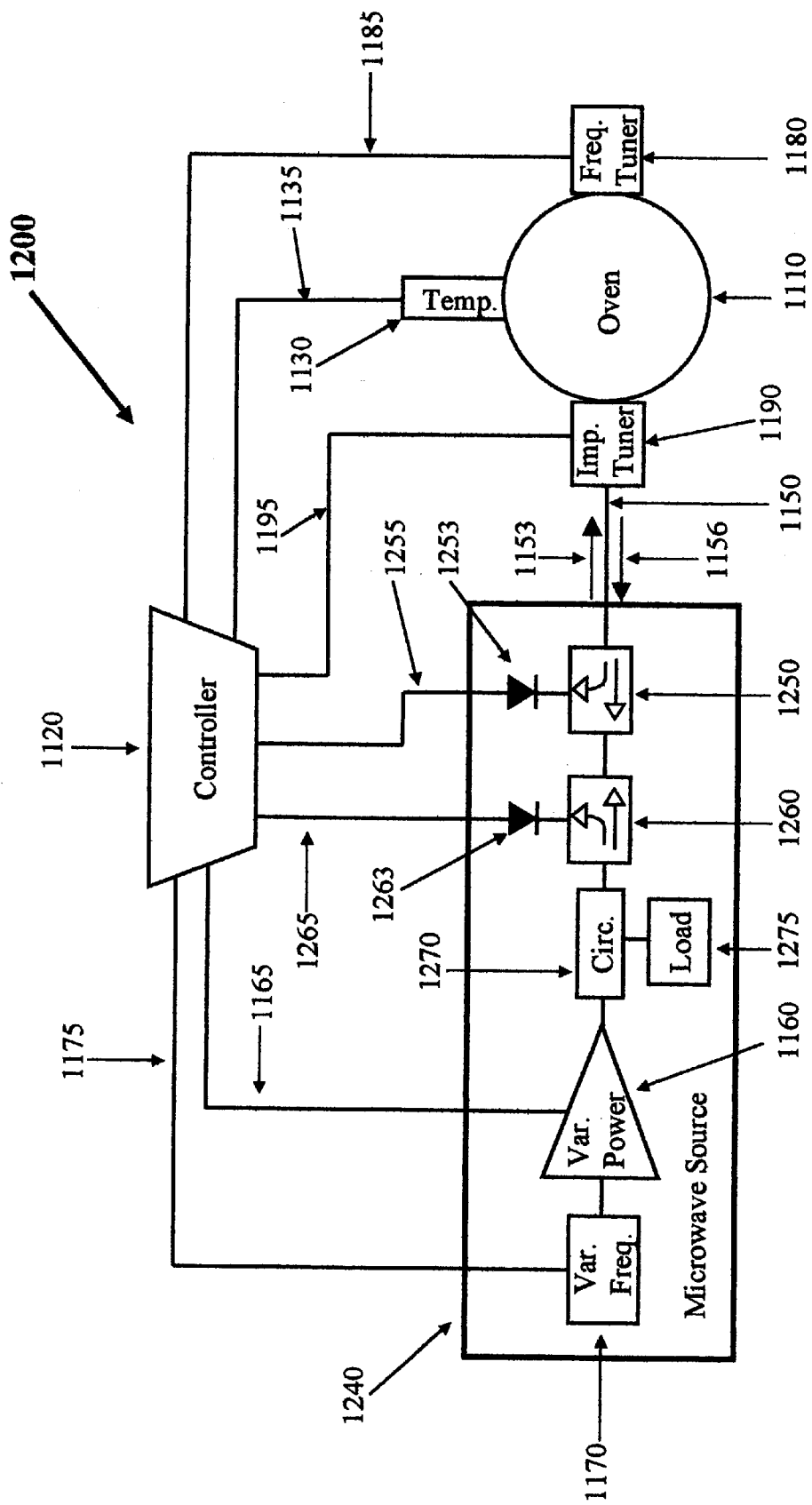
FIG. 25 shows a system which can control the temperature of a column in a chromatographic column microwave oven and which can control the efficiency of the microwave power source utilizing direct measurement of the power level of the microwave signal reflected by the oven.

The system 1200 shown in FIG. 25 includes some additional optional components beyond those in the system 1100 shown in FIG. 24 which enable the system 1200 to adjust system impedances and column temperature simultaneously by directly measuring microwave signal levels. Referring to FIG. 25, a directional coupler 1250 within the microwave source 1240 couples a small portion of the reflected microwave signal 1156 to a detector 1253 which generates a signal indicating the reflected microwave power level. This signal is transmitted to the controller 1120 by the signal line 1255. Similarly, a directional coupler 1260 samples a small portion of the microwave signal 1153 to the detector 1263 which generates a signal related to the outgoing microwave power level. This signal is transmitted to the controller 1120 by signal line 1265. Given the signals from signal lines 1255 and 1265 indicative of the reflected and outgoing power levels respectively, the controller 1120 can continuously determine how much microwave power is being transmitted into the oven 1110 and how much is being reflected back to the microwave source 1240. With this information, the controller 1120 can continually adjust the impedance match between the microwave source 1240 and the oven 1110 by tuning the variable frequency element 1170, the frequency tuning element 1180, and/or the impedance tuning element 1190 to minimize the power level of the reflected microwave signal 1156 measured by the detector 1253. As the impedance matching control loop and the column temperature control loop do not use any of the same components except for the controller 1120, these control loops can be performed simultaneously to the extent allowed by the controller 1120.

The microwave source 1240 can be damaged or destroyed if the reflected microwave signal 1156 is excessive. Including an optional circulator 1270 in the microwave source 1240 as shown in FIG. 25 can eliminate damage. The circulator 1270 redirects most of the reflected microwave signal 1156 into a matched load 1275 which dissipates the reflected microwave signal 1156 before it reaches the sensitive portions of the microwave source 1240.

Cooling the Oven

Conventional chromatographic ovens use large, high flow rate fans for cool down after a heating cycle. Even so, they do not cool down very quickly because the ovens contain so much thermal energy. Conversely, the chromatographic column microwave ovens taught herein can be cooled rapidly with a modest flow of air because the column heating elements within the ovens are heated selectively and they have very little mass. However, if cooling air does not flow quite evenly over the column heating element, then the column heating element will not cool evenly and a temperature gradient will result around the column heating element during the cooling process. If this temperature gradient is not eliminated prior to performing chromatographic analyses, lower repeatability results will be the consequence. The temperature gradient cannot be corrected quickly by heating the column heating element using the column microwave oven because the oven is designed to deliver heat energy with a fixed gradient around the column heating element. The heating gradient cannot be adjusted to compensate for uneven starting conditions. Thus, temperature gradients that result from uneven cooling will only dissipate as a result of radiative and conductive redistribution of thermal energy around the column heating bundle. These are slow processes. Consequently, the total 'cooling' time needed to establish acceptable thermal equilibrium conditions prior to starting chromatographic analyses is dramatically increased if air flow is uneven during cooling. Cooling times can increase from 45 seconds to over 180 seconds.

To achieve rapid cooling times using convection cooling, chromatographic column microwave ovens must be designed to force cooling air to flow substantially evenly around column heating elements. Within radially symmetric, cylindrical ovens, the cooling air must flow in a radially symmetric pattern. This is accomplished by using air inlets and outlets that are radially symmetric. Thus, air inlets can only be placed in the axial center of the oven or dispersed evenly about the axial center of the oven. Cooling efficiency will be determined by how efficiently the resulting air flow is forced to pass over the column heating element.

Figure 26:
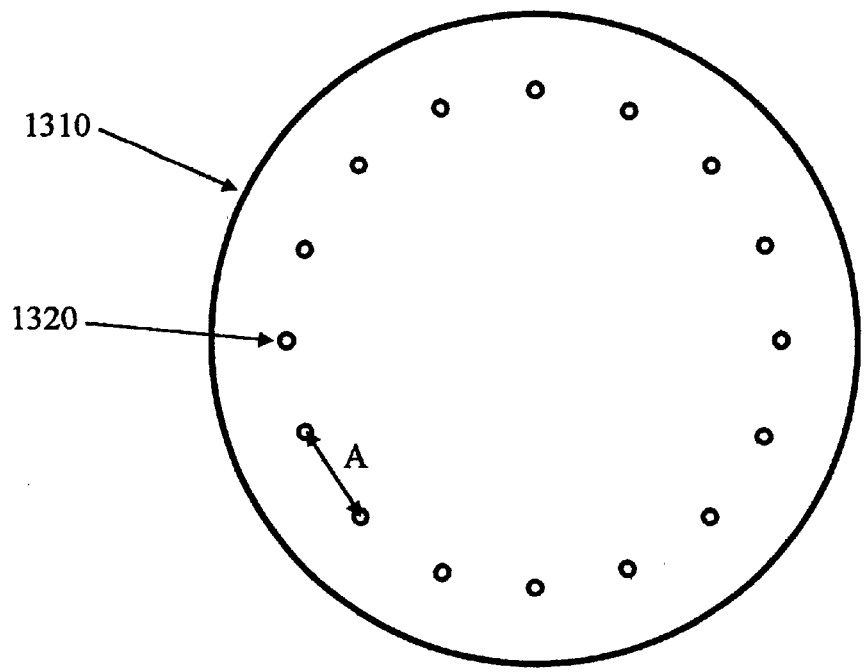
FIG. 26 shows an end cap with a large number of holes distributed symmetrically about its center.
Figure 27:
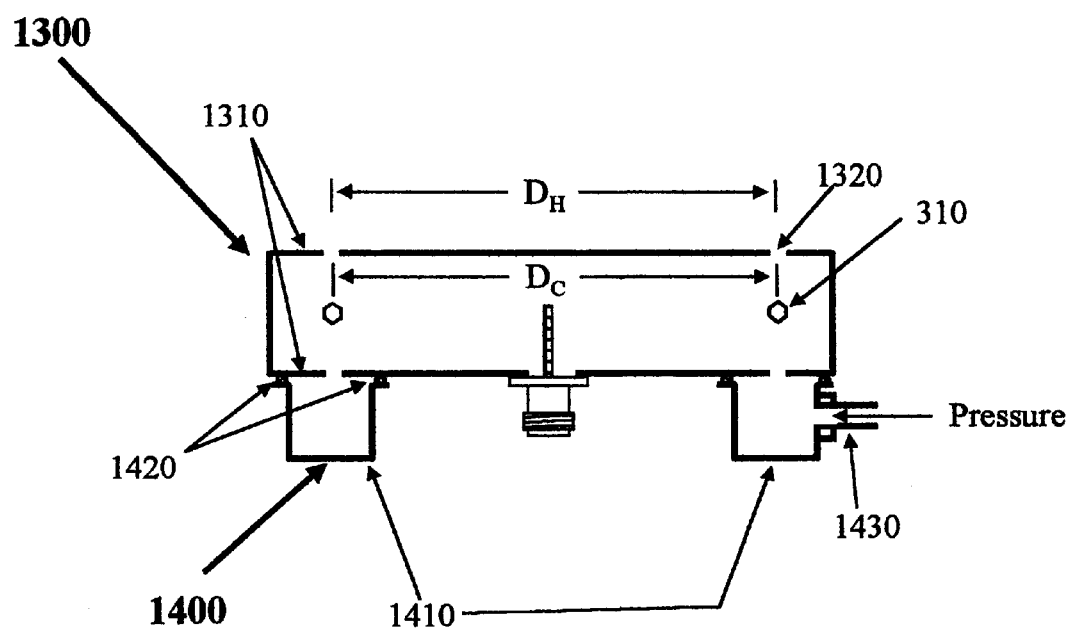
FIGS. 27 and 28 are cross-sectional views along the central axis of chromatographic column microwave ovens in which the column heating bundle can be cooled rapidly and evenly.

FIG. 26 shows an end cap 1310 that is well suited for even cooling of a chromatographic column in a chromatographic column microwave oven. The end cap 1310 has numerous holes 1320 through it that are evenly spaced about the center of the end cap 1310. The distance between adjacent holes, A, should typically be no greater than three times the internal axial height of the oven in which the end cap 1310 is used. FIG. 27 shows the cross sections an oven 1300 and an air flow assembly 1400 along their central axes. The oven 1300 is identical to the oven 300 shown in FIG. 13, though it could be any oven built in accordance with the teaching of this invention, except that the two end caps 200 in oven 300 are replaced with the two end caps 1310. The diameter $D_H$ of the circle of holes 1320 is essentially the same as the diameter $D_B$ of the column bundle 310 so as to force the air flowing axially through the oven 1300 to flow right past the column bundle 310. The air flow assembly 1400 is used to channel air to all of the holes 1320 in one end cap 1310. The air flow assembly 1400 includes a circular round channel 1410 (shown in cross section), two circular air tight seals 1420, and a pneumatic port 1430. The air flow assembly 1400 is held in place about the axial center of the oven 1300 on one end cap 1310. When configured as shown in FIG. 27, pressurized air flowing into the pneumatic port 1430 will be forced to flow substantially evenly through the holes 1320 in one end cap 1310, flow axially through the oven 1300 past the column bundle 310, and finally flow out of the oven 1300 through the holes 1320 in the second end cap 1310. The combination of the oven 1300 and the air flow assembly 1400 provides extremely efficient cooling of column bundle 310 because all the cooling air is forced to flow right around the column bundle 310. The cooling is also very quick because the air flow is substantially equal around column bundle 310 so the thermal equilibration time needed after cooling is dramatically reduced.

Figure 28:
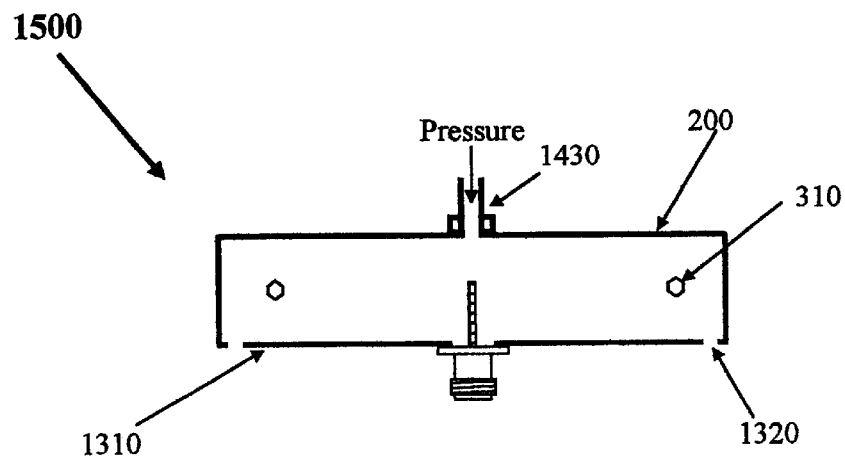

FIG. 28 shows the cross section of an oven 1500 about its central axis which is mechanically simpler than the system shown in FIG. 27, but the cooling efficiency is not as high. The oven 1500 is identical to the oven 300 shown in FIG. 13, though it could be any oven built in accordance with the teaching of this invention, except for (1) one end cap 200 is replaced with the end cap 1310 and (2) a pneumatic port 1430 is placed in the center of the end cap 200. Pressurized air flowing into the pneumatic port 1430 will flow radially outward in the oven 1300 and exit the oven 1300 through the holes 1320 in the end cap 1310. As the air flows through the oven, it will flow tangentially by the column bundle 310. The oven 1500 is likely to require a higher cooling air flow rate than is the system shown in FIG. 27 to achieve the same cooling time.

Figure 29:
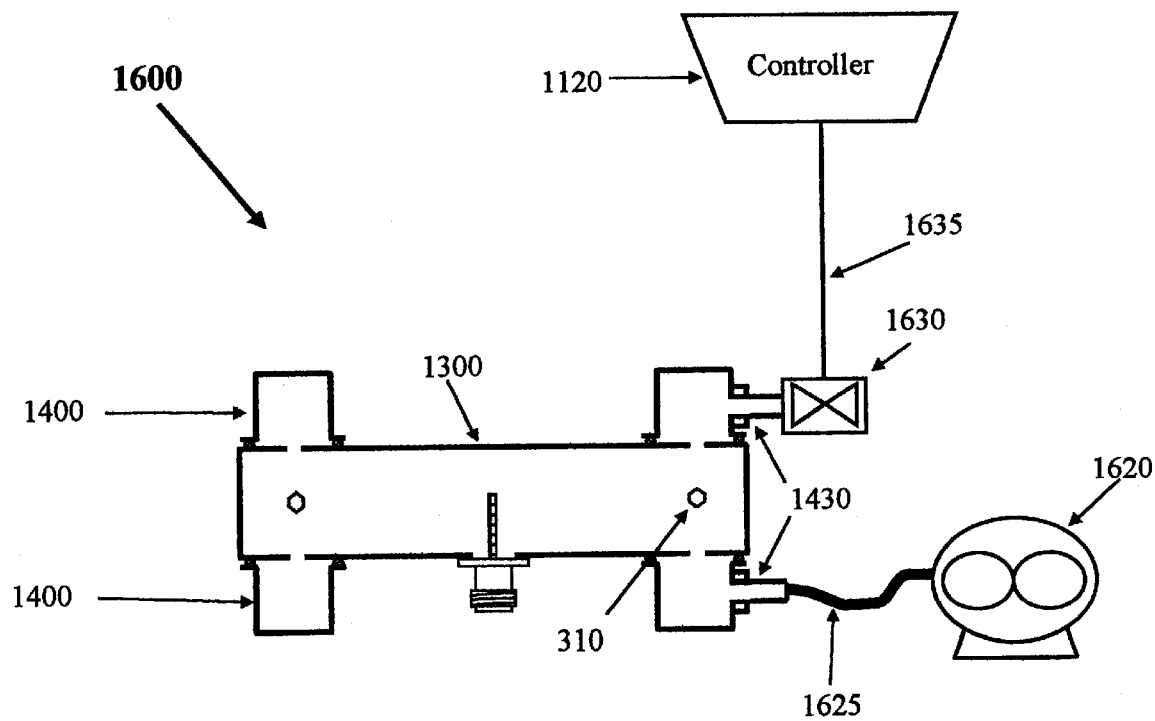
FIG. 29 shows a chromatographic column microwave oven system that can be operated in vacuum in which the column heating bundle can be cooled rapidly and evenly.

As mentioned previously, there are advantages to operating a chromatographic column microwave oven in vacuum conditions. FIG. 29 illustrates a system 1600 which can be operated in vacuum during a heating cycle and can be cooled rapidly and evenly during a cooling cycle. The system 1600 includes an oven 1300 identical to that shown in FIG. 27 onto each side of which is connected an air flow assembly 1400 identical to that shown in FIG. 27. One pneumatic port 1430 is connected to an air hose 1625 that in turn is connected to a vacuum pump 1620. The second pneumatic port 1430 is connected to a valve 1630. When a vacuum condition is to be established in the oven 1300, the valve 1630 is closed and the vacuum pump 1620 removes air from the oven 1300. When the column bundle 310 is to be cooled, the valve 1630 is opened and the vacuum pump 1620 sucks air through the oven 1300, thereby cooling the column bundle 310. If the valve 1630 is an electronic valve, it can be controlled automatically with a controller 1120 via control line 1635 such that the heating and cooling cycles are fully coordinated with the other functions of the analytical instrument into which the system 1600 is built.

Many mechanical and pneumatic configurations could be used to evenly cool a chromatographic column within a chromatographic column microwave oven as taught in this invention. Many configurations of holes could work. The holes could be placed in many locations in the oven. It should be understood that central feature of this invention as regards cooling is the usage of assemblies which induce even cooling with symmetric air flow patterns within chromatographic column microwave ovens.

Controlling the Temperature of the Oven Walls

Maximum reproducibility in chromatographic analyses requires the maximum reproducibility in the thermal condition to which a chromatographic column is exposed during the analyses. The chromatographic column microwave oven embodiments described heretofore are designed to expose the column heating elements to controlled microwave radiation so that they will be heated in a highly predictable manner. To achieve the best possible analytical reproducibility, it may however be necessary to better control the thermal environment of the column heating element as well. In this case, that means controlling the temperature of the oven walls. The temperature of the air in the oven is controlled indirectly via the oven walls and the column heating element.

Figure 30:
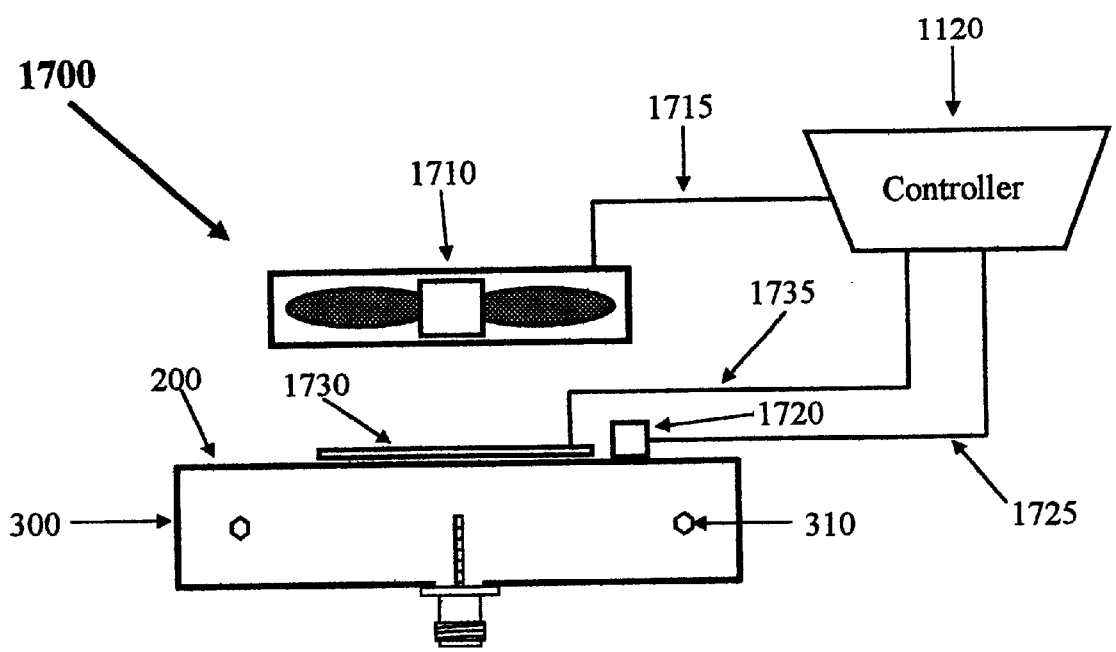
FIG. 30 shows a chromatographic column microwave oven system in which the oven skin temperature is regulated.

FIG. 30 shows a simple system 1700 with which the temperature of the oven walls can be controlled. The system 1700 includes an oven 300 which could be any oven built in accordance with the teaching of this invention, a controller 1120, a cooling fan 1710, and a temperature sensor 1720. In normal operation, the temperature of the walls of the oven 300 will be higher than the ambient temperature because of the thermal energy it dissipates when the column bundle 310 is being heated. The temperature of the walls of the oven 300 can vary over a wide range depending on the amount of microwave power being dissipated within it. The cooling fan 1710, if operated continuously, will reduce this temperature range. If the cooling fan 1710 is actively controlled, the temperature of the walls of the oven 300 can be maintained at a substantially constant set value. The temperature sensor 1720 measures the temperature of the oven walls and transmits this information to the controller 1120 on the signal line 1725. If the temperature is higher than the set value, the controller 1120 activates the fan 1710 using control line 1715. When the temperature is reduced to the set value, the controller turns the fan 1710 off again. While this simple control scheme will work, it may not always work optimally because the heating of the oven walls is indirect and not part of the control loop,. The temperature control of the oven walls in improved by using a heater 1730 to directly heat the oven walls. Controller 1120 controls the heater via control line 1735. Together, the fan 1710, the heater 1730, the temperature sensor 1720, and the controller 1120 comprise a closed-loop temperature system that can be used to regulate rapidly and accurately the temperature of the oven walls thereby improving chromatographic analysis. For simplicity, the heating and cooling functions could be combined in a thermoelectric heater.

If possible, the fan 1710 and the heater 1730 should be positioned with respect to the oven 300 such that they cool and heat in a radially symmetric pattern. The rotational axis of the fan 1710 should be lined up with the central axis of the oven 300. The heater should be placed in the center of one end cap 200 on the oven 300. This will not result in even heating and cooling of the oven walls, but it will result in repeatable and symmetric heating and cooling with respect to the column bundle 310. Moreover, if the oven walls are made of a material that has a very high thermal conductivity such as aluminum, the temperature differences around the oven walls will be small.

Many configurations and types of heaters, coolers, or temperature sensors could be used to regulate the wall temperature of a chromatographic column microwave oven. It should be understood that all such configurations and types fall within the scope of this invention.

The above disclosure sets forth a number of embodiments of the present invention. Other arrangements or embodiments, not precisely set forth, could be practiced under the teachings of the present invention and as set forth in the following claims.

We claim:

1. A microwave heating apparatus for heating a chromatographic column assembly containing a microwave absorbing material and having a coiled column with a plurality of loops extending about an axis, said apparatus comprising:

a transmitter transmitting a microwave signal from a microwave source; and a cavity containing the chromatographic column assembly, said cavity containing an electromagnetic field in response to the microwave signal, said chromatographic column assembly extending within the cavity relative to predetermined electromagnetic field strength contours to provide a predetermined heating profile along the axis of the coiled column of the chromatographic column assembly.

2. The microwave heating apparatus of claim 1 wherein the cavity comprises a resonant cavity.

3. The microwave heating apparatus of claim 2 further comprising a variable frequency tuning element to adjust the resonant frequency of the cavity.

4. The microwave heating apparatus of claim 2 further comprising a capacitive element to adjust the resonant frequency of the cavity.

5. The microwave heating apparatus of claim 1 further comprising an impedance matching element to adjust the input impedance of the microwave heating apparatus.

6. The microwave heating apparatus of claim 5 wherein the impedance matching element comprises a stub tuner having at least one adjustable stub.

7. The microwave heating apparatus of claim 1 further comprising a controller to adjustably match the input impedance of the microwave heating apparatus to the output impedance of the microwave source.

8. The microwave heating apparatus of claim 1 wherein the cavity further comprises a plurality of air inlets and outlets providing a substantially even flow of cooling air around the column assembly.

9. The microwave heating apparatus of claim 1 further comprising a temperature regulation system to control the temperature of the walls of the cavity.

10. A microwave heating apparatus for heating a chromatographic column assembly containing a microwave absorbing material and having a coiled column with a plurality of loops extending about an axis, said apparatus comprising:

a resonant cavity containing the coiled column and supporting the coiled column in a radially symmetrical arrangement about a central axis; and a transmitter transmitting a microwave signal from a microwave source into said resonant cavity to produce an electromagnetic field within said resonant cavity that is radially symmetric about the central axis and has a predetermined gradient in the axial direction, thereby providing a predetermined heating profile along the axis of the coiled column of the chromatographic column assembly.

11. The microwave heating apparatus of claim 10 further comprising a variable frequency tuning element to adjust the resonant frequency of the cavity.

12. The microwave heating apparatus of claim 10 further comprising a capacitive element to adjust the resonant frequency of the cavity.

13. The microwave heating apparatus of claim 10 further comprising an impedance matching element to adjust the input impedance of the microwave heating apparatus.

14. The microwave heating apparatus of claim 13 wherein the impedance matching element comprises a stub tuner having at least one adjustable stub.

15. The microwave heating apparatus of claim 10 further comprising a controller to adjustably match the input impedance of the microwave heating apparatus to the output impedance of the microwave source.

16. The microwave heating apparatus of claim 10 wherein the cavity further comprises a plurality of air inlets and outlets providing a substantially even flow of cooling air around the column assembly.

17. The microwave heating apparatus of claim 10 further comprising a temperature regulation system to control the temperature of the walls of the cavity.

* * * * *

UNITED STATES PATENT AND TRADEMARK OFFICE
CERTIFICATE OF CORRECTION

PATENT NO. : 6,316,759 B1
DATED : November 13, 2001
INVENTOR(S) : Gaisford et al.

Page 1 of 1

It is certified that error appears in the above-identified patent and that said Letters Patent is hereby corrected as shown below:

Column 14,
Line 59, replace "end cap 620" with -- end cap 610 --

Column 20,
Line 13, replace "signal lines 860" with -- signal wires 920 --
Line 20, replace "signal lines 920" with -- signal wires 920 --

Column 24,
Line 11, replace "diameter $D_B$" with -- diameter $D_C$ --

Column 25,
Line 49, replace "oven walls in improved" with -- oven walls is improved --

Signed and Sealed this

Thirtieth Day of April, 2002

Attest:

JAMES E. ROGAN
Attesting Officer
Director of the United States Patent and Trademark Office